(12) United States Patent
Kuo et al.

(10) Patent No.: US 9,556,218 B2
(45) Date of Patent: Jan. 31, 2017

(54) PROCESS FOR THE PREPARATION OF ABIRATERONE AND INTERMEDIATES THEREOF

(71) Applicant: ScinoPharm Taiwan, LTD., Tainan (TW)

(72) Inventors: Lung-Huang Kuo, Tainan (TW); Hsiao-Ping Fang, Tainan (TW); Ming-Feng Wu, Tainan (TW); Yu-Sheng Chang, Tainan (TW)

(73) Assignee: ScinoPharm Taiwan, Ltd., Shan-Hua, Tainan (TW)

( * ) Notice: Subject to any disclaimer, the term of this patent is extended or adjusted under 35 U.S.C. 154(b) by 69 days.

(21) Appl. No.: 14/315,642

(22) Filed: Jun. 26, 2014

(65) Prior Publication Data

US 2015/0005489 A1 Jan. 1, 2015

Related U.S. Application Data

(60) Provisional application No. 61/840,590, filed on Jun. 28, 2013.

(51) Int. Cl.
*C07J 43/00* (2006.01)
*C07J 31/00* (2006.01)
*C07J 1/00* (2006.01)

(52) U.S. Cl.
CPC ............ *C07J 43/003* (2013.01); *C07J 1/0011* (2013.01); *C07J 31/006* (2013.01); *Y02P 20/55* (2015.11)

(58) Field of Classification Search
CPC .................................................... C07J 43/003
USPC ........................................................ 540/95
See application file for complete search history.

(56) References Cited

U.S. PATENT DOCUMENTS

| | | | |
|---|---|---|---|
| 5,604,213 A | 2/1997 | Barrie et al. | |
| 2011/0288288 A1 | 11/2011 | Bury | |

FOREIGN PATENT DOCUMENTS

| | | |
|---|---|---|
| CN | 102030798 A | 4/2011 |
| CN | 103059091 A | 4/2013 |
| WO | 2006/021776 A1 | 3/2006 |
| WO | WO-2008110941 A2 | 9/2008 |
| WO | WO-2012083112 A2 | 6/2012 |
| WO | 2013/030410 A2 | 3/2013 |
| WO | 2013/030410 A3 | 3/2013 |
| WO | 2013/053691 A1 | 4/2013 |

OTHER PUBLICATIONS

Behenna, Douglas C. et al., "Simple Enantioselective Approach to Synthetic Limonoids," *J.Am. Chem. Soc.* (2008) 130(21):6720-6721.

Kang, Suk-Ku et al., "Palladium-Catalyzed Arylation of Alylic Diols: Highly Selective Synthesis of Phenyl-Substituted Allylic Diols," *Tetrahedron Letters* (1995) 36(35):6287-6290.

Potter, Gerald A. et al., "Novel Steroidal Inhibitors of Human Cytochrome $P450_{17\alpha}$ ($17\alpha$-Hydroxylase-$C_{17,20}$-lyase): Potential Agents for the Treatment of Prostatic Cancer," *J. Med. Chem.* (1995) 38(13):2463-2471.

Potter, Gerald A. et al. "A Convenient, Large-Scale Synthesis of Abiraterone Acetate [3β-Acetoxy-17-(3-Pyridyl)Androsta-5,16-Diene], A Potential New Drug for the Treatment of Prostate Cancer," *Organic Preparations and Procedures Int.* (1997) 29(1):123-134.

Sakurai, Hidehiro et al., "Pd/C as a Reusable Catalyst for the Coupling Reaction of Halophenols and Arylboronic Acids in Aqueous Media," *J. Org. Chem.* (2002) 67(8):2721-2722.

Shi, Jun et al., "Stereodivergent Synthesis of 17-α and 17-β-Aryl Steroids: Application and Biological Evaluation of DRing Cortistatin Analogues," *Angew. Chem. Int. Ed.* (2009) 48:4328-4331.

Stang, Peter J., "Single-Step Improved Synthesis of Primary and Other Vinyl Trifluoromethanesulfonates," *Synthesis-stuttgart* (1980) 1980(04):283-284.

Sun, Qian et al., "$Pd(PPh_3)_4$/AgOAc-catalyzed coupling of 17-steroidal triflates and alkynes: Highly efficient synthesis of D-ring unsaturated 17-alkynylsteroids," *Steroids* (2010) 75:936-943.

Wang, Lijun et al., "Screening Binary Systems of Chelating Agents Combined with Carbon or Silica Gel Adsorbents: The Development of a Cost-Effective Method to Remove Palladium from Pharmaceutical Intermediates and APIs," *Org. Process Res. Dev.* (2011) 15:1371-1376.

Yu, Wensheng et al., "A New Strategy for the Stereoselective Introduction of Steroid Side Chain via α-Alkox Vinyl Cuprates: Total Synthesis of a Highly Potentt Antitumor Natural Product OSW-1[1]," *J. Am. Chem. Soc.* (2001) 123(14):3369-3370.

Gravett et al., "A Suzuki coupling approach to bufadienolides," Tetrahedron Letters, 2001, vol. 42(51), pp. 9081-9084.

(Continued)

*Primary Examiner* — Brenda Coleman
(74) *Attorney, Agent, or Firm* — Mintz Levin Cohn Ferris Glovsky and Popeo, P.C.

(57) ABSTRACT

The present invention provides intermediates for preparing abiraterone, and processes for preparing abiraterone and intermediates thereof. The intermediates include a compound of formula (IV):

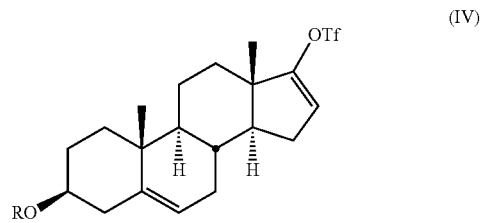

(IV)

wherein R represents a hydroxy-protecting group.

17 Claims, 11 Drawing Sheets

(56) References Cited

OTHER PUBLICATIONS

Yu et al., "A facile generation of enolates from silyl enol ethers by potassium ethoxide," Tetrahedron Letters, 2001, vol. 42(3), pp. 369-372.
International Search Report and Written Opinion, Mar. 15, 2015, PCT application No. PCT/IB2014/002020, 10 pages.
Office Action for Chinese Application No. 201480037231.8, dated Jun. 27, 2016. [English translation and original].

Scheme 1: The Synthetic Route Shown in U.S. Patent No. 5,604,213

Scheme 2: Preparation of Vinyl Triflate 2 Shown in WO2006021776A1

Scheme 3: Formation of Abiraterone Acetate MsOH Salt Shown in WO2006021776A1

Scheme 4: Formation of Abiraterone Acetate CF₃SO₃H Salt Shown in CN102030798A

Scheme 5: The Synthetic Route Shown in U.S. Patent No. 5,604,213

Scheme 6: The Synthetic Route Shown in WO2013030410A2

Scheme 7: The Synthetic Route Shown in WO2013053691A1.

Scheme 8: The Synthetic Route Shown in *Steroids*, 2010, 75, 936-943.

Scheme 9. Formation of Compounds of Formula (IV)

Scheme 10. Formation of Abiraterone of Formula (I)

Scheme 11. Suzuki Coupling of Vinyl Triflate of Formula (IV) with 3-Pyridylboronic acid of Formula (VI'')

Scheme 12. Suzuki Coupling of Vinyl Triflate of Formula (V) with 3-Pyridylboronic acid of Formula (VI'')

Scheme 13. Formation of Abiraterone Acetate of Formula (I')

Synthesis scheme for compounds of formula (III-a to III-d and IV-a to IV-d)

Synthesis scheme for the formation of Abiraterone of Formula (I)

Synthesis scheme for Suzuki coupling of vinyl triflates of formula (IV-a-d) with 3-Pyridylboronic acid of Formula (VI'')

Synthesis scheme for Suzuki coupling of vinyl triflate of formula (V)

with 3-Pyridylboronic acid of Formula (VI'')

Synthesis scheme for a one pot preparation of compound of formula (I)

PROCESS FOR THE PREPARATION OF ABIRATERONE AND INTERMEDIATES THEREOF

CROSS-REFERENCES TO RELATED APPLICATIONS

This application is an application claiming benefit under 35 U.S.C. §119(e) of U.S. Provisional Patent Application No. 61/840,590 filed Jun. 28, 2013, the content of which is hereby incorporated by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates to novel processes of obtaining abiraterone and derivatives, such as abiraterone acetate, in high yield and purity, as well as to novel intermediates useful in the processes.

Abiraterone acetate, the active ingredient of ZYTIGA® is the acetyl ester of abiraterone which is an inhibitor of CYP17 (17α-hydroxylase/C17,20-lyase). Abiraterone acetate is designated chemically as (3β)-17-(3-pyridinyl)androsta-5,16-dien-3-yl acetate and its structure is:

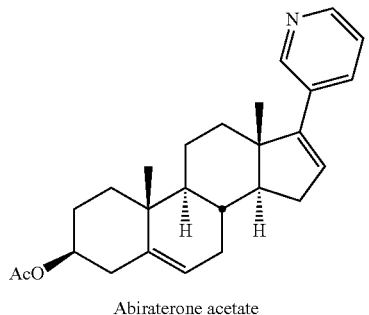

Abiraterone acetate

Abiraterone acetate is manufactured by Johnson and Johnson under the brand name ZYTIGA®. An antiandrogen which is a prodrug of abiraterone, abiraterone acetate is administered as a 250 mg tablet treating metastatic castration-resistant prostate cancer. Phase III clinical trials were started in September 2010, and the results showed an overall survival rate increase of 3.9 months. Subsequently, abiraterone acetate was approved by the FDA in April 2011 after an expedited six-month review. By March 2012, production of abiraterone acetate was in excess of 2.5 tons with worldwide sales of more than $400 million.

Abiraterone acetate was discovered by Gerry Potter in 1990 at the Cancer Research UK Centre for Cancer Therapeutics within the Institute of Cancer Research in London. Commercialization rights to abiraterone acetate were assigned to British Technology Group (BTG plc), a UK company. An early route to abiraterone acetate is shown in FIG. 5 (Scheme 1, see, U.S. Pat. No. 5,604,213). Briefly, prasterone acetate 1 was treated with triflic anhydride (Tf₂O) in dichloromethane (DCM) in the presence of 2,6-di-tert-butyl-4-methylpyridine (DTBMP) and afforded crude vinyl triflate 2. The resulting crude product mixture was purified via column chromatography packed with silica gel followed by recrystallization from n-hexane to provide purified vinyl triflate 2 in 58% yield. Subsequent Suzuki coupling between vinyl triflate 2 and diethyl(3-pyridyl)borane 3 was accomplished in the presence of a catalytic amount of bis(triphenylphosphine)palladium(II) dichloride (Pd(PPh₃)₂Cl₂). The resulting crude product mixture was purified via silica gel column chromatography, followed by recrystallization from n-hexane. The desired abiraterone acetate was obtained in 84% yield.

Subsequent efforts were directed to isolating vinyl triflate 2 without using column chromatography (see WO2006021776A1, see FIG. 6, Scheme 2). At the same time, expensive DTBMP was replaced with a readily available base (2,6-lutidine, Et₃N, or DIPEA). Despite this effort, conversion of prasterone acetate 1 was achieved in only moderate yield. As indicated by HPLC, the crude product mixture comprised about 60% of vinyl triflate 2 and about 20% of unreacted prasterone acetate 1 along with a certain amount of triene 4.

Both prasterone acetate 1 and triene 4 were difficult to remove effectively via recrystallization. The crude vinyl triflate 2 mixture was then directly taken to the subsequent Suzuki coupling with diethyl(3-pyridyl)borane 3 without purification. The resulting crude product mixture was determined to contain abiraterone acetate and unreacted prasterone acetate 1 in about a 3/1 ratio, but also containing a certain amount of triene 5. Again, both prasterone acetate 1 and diene 5 were difficult to remove efficiently via recrystallization.

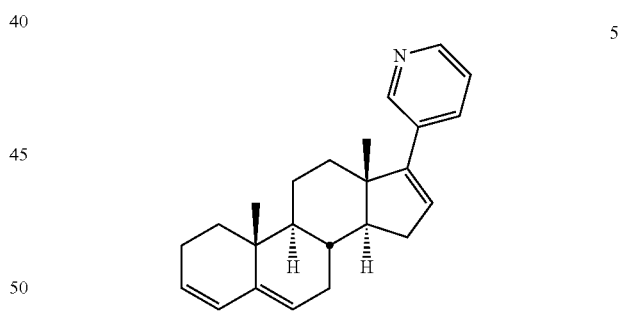

BTG plc reported, however, that both prasterone acetate 1 and triene 5 could be purged successfully via a salt formation step (WO2006021776A1). The acid counterpart could be selected from hydrochloric, sulfuric, toluoyltartaric, or methanesulfonic acid (MsOH). Abiraterone acetate MsOH salt was shown to provide the best results among the four salts evaluated. Abiraterone acetate MsOH salt was preferentially prepared from a mixture of MTBE and EtOAc (FIG. 7, Scheme 3). After recrystallization from isopropyl alcohol (IPA), the purified abiraterone acetate MsOH salt was obtained in about 33% overall yield and purity was improved from 87.7% to 96.4%.

Wanle Pharmaceutical (CN102030798A) disclosed a closely related approach using trifluoromethanesulfonic acid (CF₃SO₃H) in place of MsOH, producing the corresponding abiraterone acetate CF$_3$SO$_3$H salt (FIG. 8, Scheme 4). Abiraterone acetate CF$_3$SO$_3$H salt was also preferentially prepared from a mixture of MTBE and EtOAc. The resulting recrystallized abiraterone acetate CF$_3$SO$_3$H salt was first neutralized with Na$_2$CO$_{3(aq)}$ followed by recrystallization from n-hexane to generate the desired abiraterone acetate.

A different approach avoiding the use of expensive hindered base (DTBMP) as well as noxious Tf$_2$O was described by starting with prasterone 6 as shown in FIG. 9, Scheme 5 (see U.S. Pat. No. 5,604,213 and WO 95/09178). Prasterone 6 in EtOH was combined with hydrazine monohydrate (H$_2$NNH$_2$—H$_2$O) in the presence of a catalytic amount of hydrazine sulfate (H$_2$NNH$_2$—H$_2$SO$_4$) and led to hydrazone 7 in 98% yield. Vinyl iodide 8 was afforded in 90% yield after hydrazone 7 and 1,1,3,3-tetramethylguanidine (TMG) in a mixture of Et$_2$O and THF was treated with I$_2$.

The Suzuki reaction between vinyl iodide 8 and diethyl (3-pyridyl)borane 3 could also be achieved in the presence of a catalytic amount of Pd(PPh$_3$)$_2$Cl$_2$. However, the reaction was very slow and required 2-4 days for completion. The resulting product mixture contained about 5% of dimer 10. Abiraterone 9 with a desired purity level was produced in 57% after sequential recrystallization from a mixture of MeCN/MeOH and toluene/MeOH. Crude abiraterone acetate was afforded after abiraterone 9 was treated with acetic anhydride (Ac$_2$O) in pyridine. Reverse phase column chromatography was still required to remove the corresponding dimer 11.

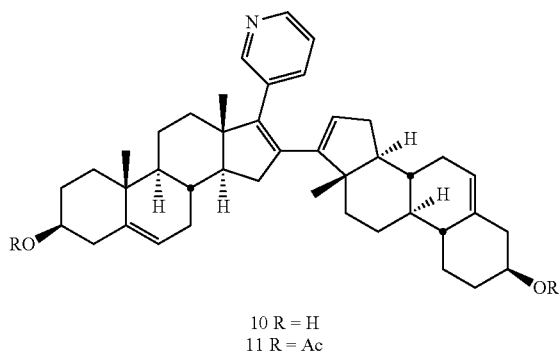

10 R = H
11 R = Ac

Crystal Pharm (WO2013030410A2) disclosed an alternative approach leading to abiraterone 9 (FIG. 10, Scheme 6). By starting with prasterone 6, vinyl iodide 8 was obtained in 86% yield over two steps based on conditions provided in U.S. Pat. No. 5,604,213 (FIG. 9, Scheme 5). The hydroxy group in vinyl iodide 8 was transformed into its corresponding tert-butyldimethylsilyl (TBS) ether 12 in 90% yield. To silyl ether 12 was added n-BuLi under cryogenic conditions (-78° C.), and the corresponding vinyl lithium intermediate was trapped with triethyl borate followed by hydrolysis affording vinyl boronic acid 13 in 81% yield over two steps. Vinyl boronic acid 13 was coupled with 3-bromopyridine in the presence of a suitable base and a catalytic amount (6 mole %) of dichloro[1,1'-bis(diphenylphosphino)ferrocene]-palladium (II) (Pd(dppf)Cl$_2$)-DCM in a mixture of THF and H$_2$O at reflux temperature (ca. 70° C.). After the reaction was completed, the mixture was concentrated and diluted with EtOAc followed by addition of aqueous HCl solution affording abiraterone 9. Subsequently, the resulting abiraterone 9 HCl salt was isolated in 70% yield (49% overall yield from prasterone 6) with unknown purity.

Zach System (WO2013053691A1, see FIG. 11, Scheme 7) describes an improved method for the preparation of abiraterone 6 via prasterone formate 14, which is closely related to BTG's process. Prasterone 6 was treated with formic acid to give prasterone formate 14 quantitatively. Prasterone formate 14 was reacted with Tf$_2$O in DCM in the presence of 2,6-lutidine afforded crude vinyl triflate 15. The reaction occurs with 80-85% conversion rate yielding 70-75% of vinyl triflate 15, 15-20% of unreacted prasterone formate 14, and <3% of diene 16. The crude mixture was taken to Suzuki cross-coupling with diethyl(3-pyridyl)borane 3 in the presence of Pd(PPh$_3$)$_2$Cl$_2$ affording crude abiraterone formate 17. The resulting mixture was hydrolyzed with 10% NaOH$_{(aq)}$ in MeOH leading to crude abiraterone 9. Purification of crude abiraterone 9 was achieved in DCM/MeOH, and the resulting purified abiraterone 9 was generated in about 50% overall yield from prasterone 6. Subsequent acetylation of abiraterone 9 was affected in a very straight forward manner to produce abiraterone acetate in 90% yield.

CRC Center (the same applicant as U.S. Pat. No. 5,604, 213) noted in *Organic Preparations and Procedures Int.*, 29 (1), 123-134 (1997), see Scheme 5 that the palladium catalyzed cross-coupling reaction of vinyl iodide 8 with diethyl(3-pyridyl)borane 3 proceeds without the protection the 3-hydroxy function to give the abiraterone (I), whereas the use of an enol triflate (i.e. prasterone vinyl triflate (V)) in the coupling reaction did not allow this option.

Vinyl triflate 19 formation with nearly quantitative yield can be achieved by adding KHMDS (0.5M in toluene) to a hydroxy group protected prasterone 18 and PhNTf$_2$ in THF has been reported in *Steroids*, 2010, 75, 936-943, see FIG. 12, Scheme 8. In this disclosed process, prasterone 18 is protected with a highly toxic protecting group (methoxymethyl, MOM, generated from carcinogen chloromethyl methyl ether (MOMCl)) which limits its use in the pharmaceutical industry. In addition, the reaction conditions of this disclosed process must be below -78° C. Moreover, the product needs to be isolated using column-chromatography.

What is needed in the art is an efficient method of preparing abiraterone and its derivatives that addresses the difficulties described by others. The present invention addresses this need, finding for example, that the use of prasterone vinyl triflate (V) in the coupling reaction is workable. Other improvements for abiraterone (I) preparation are also provided herein.

BRIEF SUMMARY OF THE INVENTION

In one aspect, the present invention provides a process for preparing a compound of formula (IV):

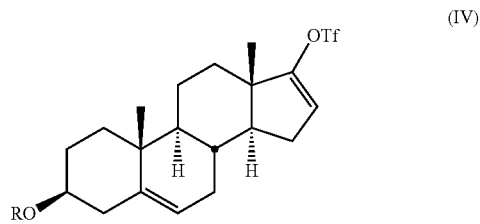

(IV)

wherein R represents a hydroxy-protecting group.

The process includes:

a) converting a compound of formula (II)

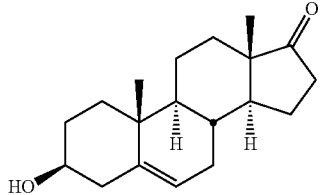

into a compound of formula (III)

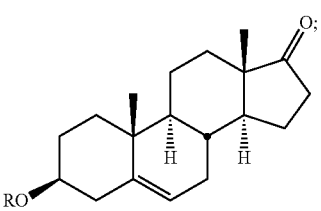

and b) reacting a compound of formula (III) with a triflating agent followed by a strong base to give a compound of formula (IV).

In another aspect, the present invention provides a process for preparing abiraterone of formula (I):

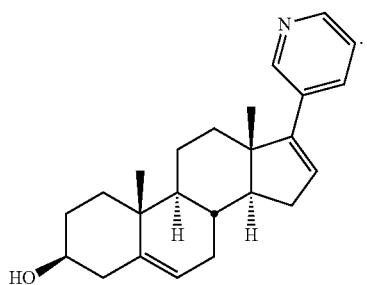

The process includes:

(a) converting a compound of formula (II)

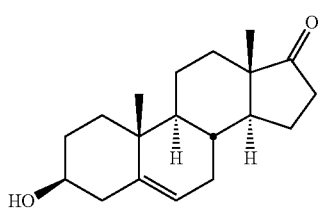

into a compound of formula (III)

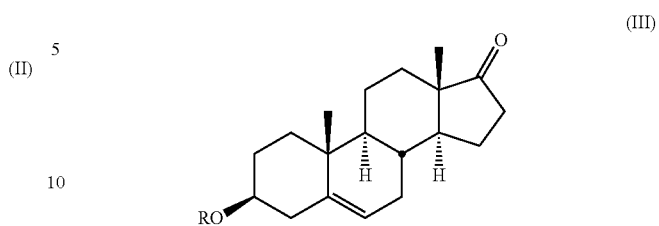

wherein R represents a hydroxy-protecting group;

(b) reacting the compound of formula (III) with a triflating agent followed by a strong base to give a compound of formula (IV)

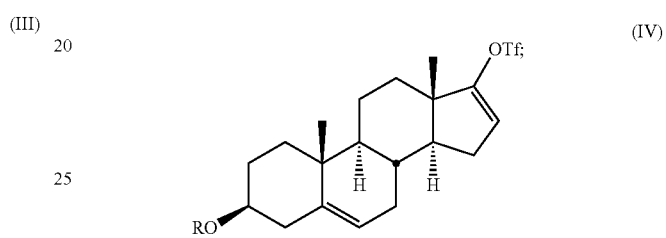

(c) deprotecting a compound of formula (IV) to give a compound of formula (V)

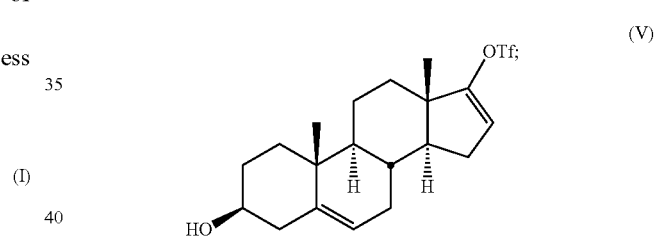

and (d) coupling a compound of the formula (V) with a compound of formula (VI)

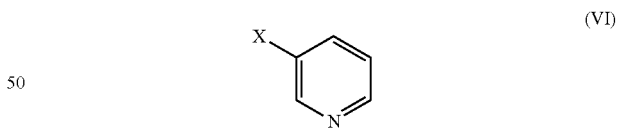

wherein X represents a boryl group, to provide abiraterone of formula (I).

In accordance with a preferred embodiment of the present invention described above, for a compound of formula (VI) which is used in step (d), X represents a boryl group, which can be a —$BY_2$ group, wherein each Y is selected from an alkyl, an alkoxy or a hydroxy group. More preferably, each Y is an ethyl or a hydroxy group.

The coupling in step (d) is carried out in the presence of palladium catalyst in an organic solvent. In certain embodiments, the palladium catalyst is selected from bis(triphenylphosphine)palladium(II) dichloride ($PdCl_2(PPh_3)_2$), tetrakis (triphenylphosphane)-palladium ($Pd(PPh_3)_4$), tris (dibenzylideneacetone)dipalladium ($Pd_2(dba)_3$), palladium acetate ($Pd(OAc)_2$), dichloro(1,2-bis(diphenylphosphino)

ethane)palladium(II) (PdCl$_2$(dppe)$_2$), 1,1'-bis(diphenylphosphino)ferrocene-palladium(II)dichloride dichloromethane (PdCl$_2$(dppf).CH$_2$Cl$_2$), bis(benzonitrile)palladium chloride (Pd(PhCN)$_2$Cl$_2$), bis(acetonitrile)palladium(II) chloride (Pd (CH$_3$CN)$_2$Cl$_2$), or combinations thereof. More preferably, the palladium catalyst is bis(triphenylphosphine)palladium (II) dichloride (PdCl$_2$(PPh$_3$)$_2$). The organic solvent can be tetrahydrofuran (THF), acetonitrile (MeCN), ethanol, 2-methyl tetrahydrofuran (Me-THF), toluene (PhMe), or a mixture of two or more of these solvents, or one or more of these solvents combined with water.

The coupling in step (d) also proceeds in the presence of a base. Preferably, the base is selected from sodium carbonate, potassium carbonate, sodium phosphate, potassium phosphate, sodium bicarbonate, potassium bicarbonate, or combinations thereof.

In accordance with a preferred embodiment of the present invention, the abiraterone of formula (I) obtained from the above process is further converted into abiraterone acetate of formula (I')

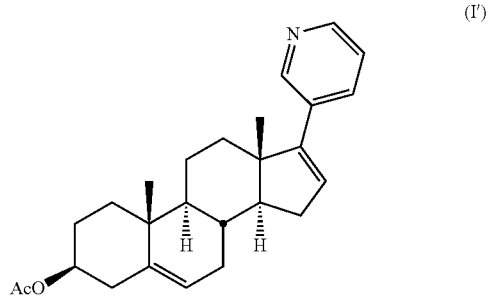

(I')

by treating (I) with an acylating reagent, which is preferably an acetic anhydride (Ac$_2$O) or an acetyl chloride, more preferably, the acylating reagent is acetic anhydride (Ac$_2$O). The acylating reaction is performed in the presence of a base which is selected from the group consisting of 4-dimethylaminopyridine (DMAP), triethylamine (Et$_3$N), N-ethyldiisopropylamine (DIPEA) and pyridine. More preferably, the base is 4-dimethylaminopyridine (DMAP).

In accordance with another aspect of the present application, the invention provides a purification process which further comprises purification of abiraterone acetate of formula (I') by:

a) providing a solution of abiraterone acetate in an organic solvent;
b) heating the solution;
c) isolating the crystalline form of abiraterone acetate, and
d) drying the isolated crystalline form of abiraterone acetate.

This process results in increased purity of abiraterone acetate (I'). Preferably, the organic solvent is selected from the group consisting of n-hexane, n-heptane, cyclohexane, acetone, acetonitrile (MeCN), dimethylsulfoxide (DMSO), methanol, ethanol, or a mixture of two or more of these solvents, or one or more of these solvent combined with water. More preferably, the solvent is a mixture of cyclohexane and water.

The various features which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE INVENTION

I. General

Figure 1:
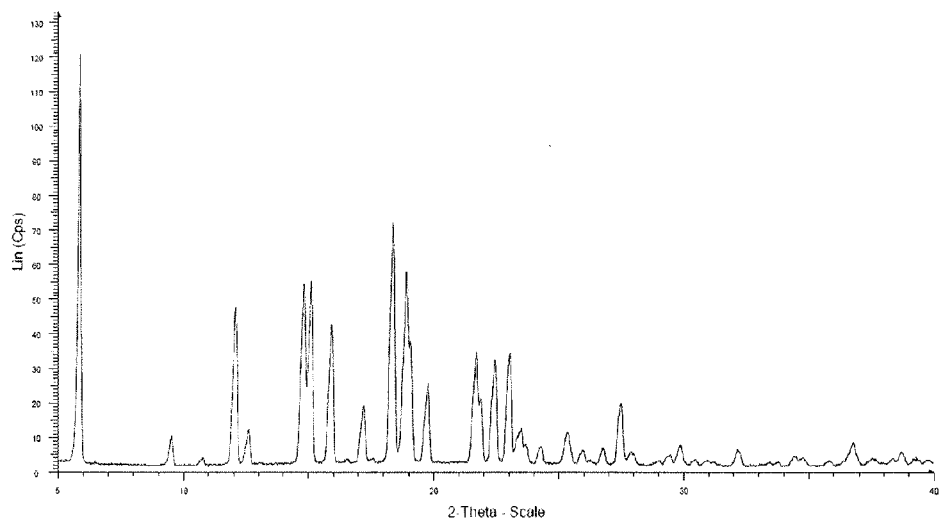
FIG. 1 is the schematic diagram showing the X-ray powder diffraction (XRPD) pattern of abiraterone acetate of formula (I').

The present invention is directed to novel processes of obtaining abiraterone and its derivatives, such as abiraterone acetate, in high yield and purity, as well as to novel intermediates useful in these processes.

II. Definitions

As used herein, the terms "aryl" and "aromatic ring," by themselves or as part of another substituent, refer to a polyunsaturated, hydrocarbon group which can be a single ring or multiple rings (up to three rings) which are fused together or linked covalently. Non-limiting examples of aryl groups include phenyl, naphthyl and biphenyl. "Substituted aryl" groups can be substituted with one or more groups selected from halo, hydroxy, amino, alkylamino, amido, acyl, nitro, cyano, and alkoxy.

The term "alkyl," by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 10 carbon atoms. For example, an alkyl group can contain 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the terms "contacting" and "reacting" refers to the process of bringing into contact at least two distinct species such that they can form a new product. It should be appreciated, however, that the resulting reaction product can be produced directly from a reaction between the added reagents or from an intermediate from one or more of the added reagents that can be produced in the reaction mixture. As used herein, the term "treating" refers to contacting a substance with at least one other substance.

As used herein, the "boryl group" refers to a moiety having the formula —BR'R", wherein R' and R" are independently selected from hydrogen, hydroxy, alkyl groups, and aryl groups, as defined herein. In general, compounds having boryl groups are boranes characterized by at least one carbon-boron bond. Boranes include, but are not limited to, boronic acids, alkyl boranes, alkenyl boranes, and vinyl boranes. A borane can be formed, for example, via reaction of a compound having a formula R'R"BH with a suitable parent molecule such as an alkene. A borane derivative can be isolated and purified before conversion into another compound, or it can be used in situ without isolation and purification.

As used herein, the term "protecting group" refers to a moiety that is formed to render a functional moiety less reactive or unreactive. Forming the moiety is referred to as "protecting" the functional moiety or the molecule that contains the functional moiety. The protecting group can be removed so as to restore the functional moiety to its original state. Removing the protecting group is referred to as "deprotecting." Various protecting groups and protecting reagents, including hydroxy protecting groups, are well known to one of ordinary skill in the art and include compounds that are disclosed in *Protective Groups in Organic Synthesis,* 4th edition, T. W. Greene and P. G. M. Wuts, John Wiley & Sons, New York, 2006, which is incorporated herein by reference in its entirety.

As used herein, the term "triflating agent" refers to a compound that is useful in a reaction in which a triflate group is attached to a hydroxy group to form a triflate ester. The triflating agent is the source of the trifluoroacetyl group. Triflating agents include, but are not limited to triflic anhydride, N-phenyl-bis(trifluoromethanesulfonimide) (PhNTf$_2$), N-(5-chloro-2-pyridyl)triflimide and N-(2-pyridyl)triflimide.

As used herein, the term "solvent" refers to a substance that is liquid at ambient temperature and pressure. Examples of solvents include water, acetone, toluene, methylene chloride, ethyl acetate, acetonitrile, tetrahydrofuran, benzene, chloroform, diethyl ether, dimethyl formamide, dimethyl sulfoxide, and petroleum ether.

As used herein, the term "halogen" refers to fluorine, chlorine, bromine, and iodine. The term "halide" refers to a compound containing a halogen or an anion originating from a parent halogen.

As used herein, the term "base" refers to a molecule that is capable of accepting a proton (i.e., a hydrogen cation) to form a conjugate acid of the base. Examples of bases include, but are not limited to, Huenig's base (i.e., N,N-diisopropylethylamine), lutidines including 2,6-lutidine (i.e., 2,6-dimethylpyridine), triethylamine, and pyridine. Examples of strong bases include, but are not limited to, amide-based organometallic reagents such as lithium diisopropylamide or lithium bis(trimethylsilyl)amide.

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed. The following schemes are provided as embodiments to illustrate, but not to limit the present invention.

III. Embodiments of the Invention

In one aspect, a process is provided for preparing a compound of formula (IV),

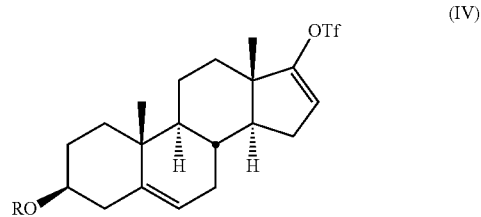

(IV)

wherein R represents a hydroxy-protecting group, comprising:

a) converting a compound of formula (II)

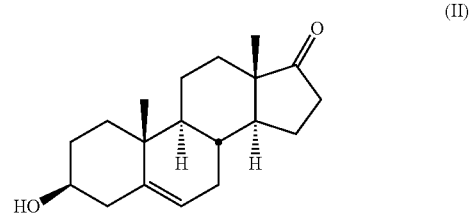

(II)

into a compound of formula (III)

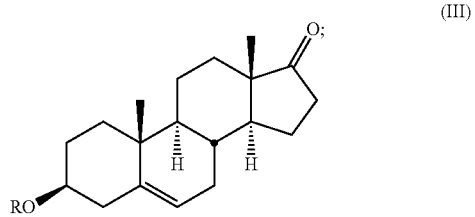

and b) reacting a compound of formula (III) with a triflating agent followed by a strong base to give a compound of formula (IV).

Figure 13:
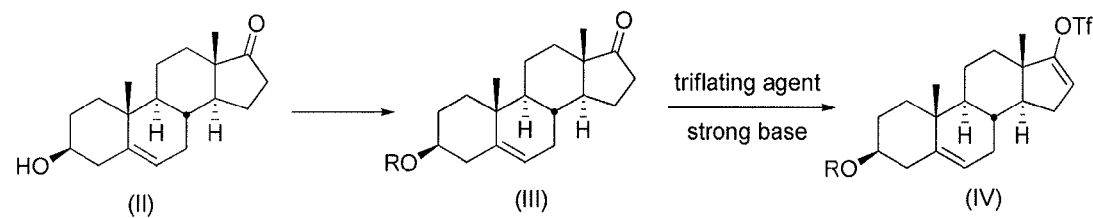
FIG. 13 provides Scheme 9 illustrating the formation of compounds of formula (IV).

In some embodiments, an efficient preparation of the vinyl triflate of formula (IV) starts with prasterone of formula (II) and proceeds in about 90% yield over two steps (FIG. 13, Scheme 9). Notably, tedious and costly column chromatography steps are excluded completely, and production throughput is greatly improved.

The hydroxy group in prasterone of formula (II) can be individually reacted with hydroxy protecting reagents including trimethylsilyl chloride (TMSCl), tert-butyldimethylsilyl chloride (TBSCl), 3,4-dihydro-2H-pyran (DHP), triethylsilyl chloride (TESCl), triisopropylsilyl chloride (TIPSCl), dimethylphenylsilyl chloride, diphenylmethylsilyl chloride, tert-butylphenylsilyl chloride (TBDPSCl), and trityl chloride (TrCl), to provide the compound of formula (III) with a hydroxy protecting group (R) which can be trimethylsilyl (TMS), tert-butyldimethylsilyl (TBS), tetrahydropyranyl (THP), triethylsilyl (TES), triisopropylsilyl (TIPS), dimethyphenylsilyl, diphenylmethylsilyl, tert-butyldiphenylsilyl (TBDPS) and triphenylmethyl (trityl, Tr). In some embodiments, the hydroxy protecting group is trimethylsilyl (TMS). The corresponding compound of formula (III) can be isolated via either solvent replacement or directly taken to the downstream step after concentration to remove volatile side products.

The triflating step (converting a compound of formula (III) into a compound of formula (IV)) can be conducted by dissolving the compound of formula (III) with a triflating agent, such as N-phenyl-bis(trifluoromethanesulfonimide) (PhNTf$_2$), N-(5-chloro-2-pyridyl)triflimide or N-(2-pyridyl) triflimide in a suitable solvent. In selected embodiments, the triflating agent is N-phenyl-bis(trifluoromethanesulfonimide) (PhNTf$_2$). In other selected embodiments, the solvent used in the reaction of converting the compound of formula (III) into the compound of formula (IV) is selected from the group consisting of tetrahydrofuran (THF), 2-methyl tetrahydrofuran (Me-THF), xylene, toluene and combinations thereof. In still other selected embodiments, the solvent is THF. The reaction is then followed by addition of a strong base. In one group of embodiments, the strong base is an amide based organometallic reagent. For example, the amide based organometallic reagent can be selected from lithium bis(trimethylsilyl)amide (LiHMDS), sodium bis(trimethylsilyl)amide (NaHMDS), potassium bis(trimethylsilyl)amide (KHMDS) and lithium diisopropylamide (LDA) to generate the corresponding vinyl triflate of formula (IV) in 85-95% yield. In certain embodiments, the amide based organometallic reagent is sodium bis(trimethylsilyl)amide (NaHMDS).

Figure 14:
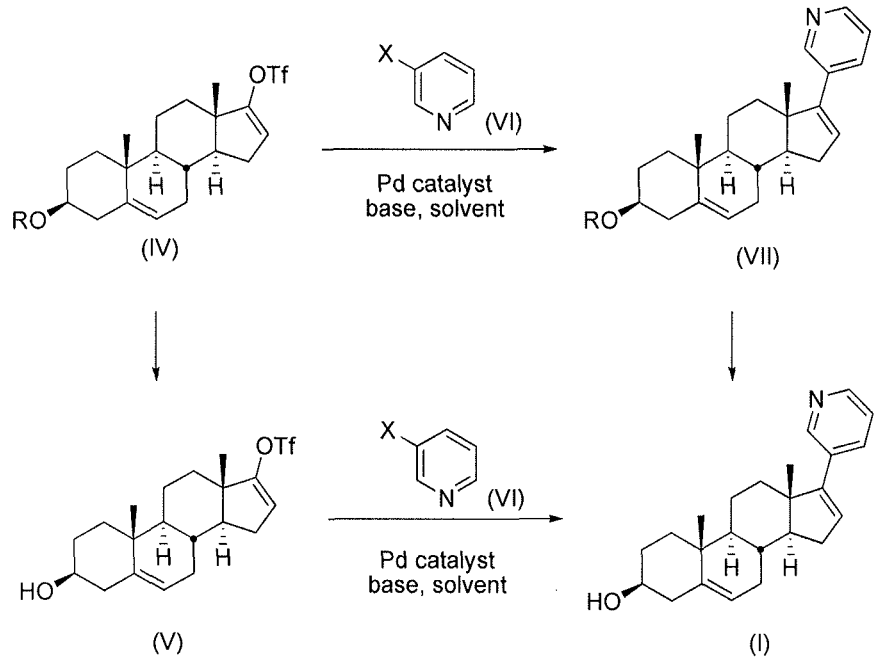
FIG. 14 provides Scheme 10 illustrating the formation of Abiraterone of Formula (I).

In another embodiment, after aqueous workup, the vinyl triflate of formula (IV) can be reacted with a 3-pyridylborane derivative of formula (VI),

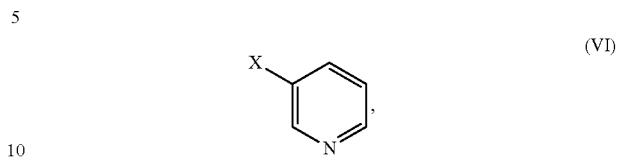

wherein X is —BY$_2$, wherein Y is an alkyl, alkoxy or hydroxy group, in a 'Suzuki coupling' in the presence of a palladium catalyst with a base in an organic solvent with or without isolation of the vinyl triflate of formula (IV) in Scheme 9 (FIG. 13) to provide a compound of formula (VII) (see FIG. 14, Scheme 10).

Suzuki couplings employed in the present invention generally involve carbon-carbon bond formation via palladium-catalyzed couplings of boronic acids, boronic acid derivatives or boryl compounds with suitably-functionalized organic substrates. Examples of suitably-functionalized organic substrates include, but are not limited to, aryl halides, alkenyl halides, aryl triflates, and alkenyl triflates. Boronic acid derivatives include, but are not limited to, potassium trifluoroborates, organoboranes, and boronate esters. A number of palladium-based catalysts and solvents can be employed under a variety of conditions.

In some embodiments, each Y is an ethyl or hydroxy group.

In other selected embodiments, the 3-pyridylborane derivative of formula (VI) is diethyl(3-pyridyl)borane or 3-pyridylboronic acid.

In still other selected embodiments, the palladium catalyst is selected from the group consisting of bis(triphenylphosphine)palladium(II) dichloride (PdCl$_2$(PPh$_3$)$_2$), tetrakis(triphenylphosphane)palladium (Pd(PPh$_3$)$_4$), tris(dibenzylideneacetone)dipalladium (Pd$_2$(dba)$_3$), palladium acetate (Pd (OAc)$_2$), dichloro(1,2-bis(diphenylphosphino)ethane) palladium(II) (PdCl$_2$(dppe)$_2$), 1,1'-bis(diphenylphosphino) ferrocene-palladium(II)dichloride dichloromethane (PdCl$_2$ (dppf).CH$_2$Cl$_2$), bis(benzonitrile)palladium chloride (Pd (PhCN)$_2$Cl$_2$) and bis(acetonitrile)palladium(II) chloride (Pd (CH$_3$CN)$_2$Cl$_2$) or the like. In yet other embodiments, the palladium catalyst is bis(triphenylphosphine)palladium(II) dichloride (PdCl$_2$(PPh$_3$)$_2$).

A variety of bases can be used in the Suzuki coupling, including bases selected from: metal carbonates such as an alkali metal carbonate (e.g., sodium carbonate (Na$_2$CO$_3$) or potassium carbonate (K$_2$CO$_3$)); metal phosphates such as an alkali metal phosphate (e.g., sodium phosphate (Na$_3$PO$_4$) or potassium phosphate (K$_3$PO$_4$)); a metal bicarbonate such as an alkali metal bicarbonate (e.g., sodium bicarbonate (NaHCO$_3$) or potassium bicarbonate (KHCO$_3$)); and combinations thereof.

In some embodiments, the organic solvent is selected from tetrahydrofuran (THF), acetonitrile (MeCN), ethanol, 2-methyl tetrahydrofuran (Me-THF), toluene (PhMe), and combinations thereof. In some embodiments, the solvent is optionally combined with water.

After being purified via flash column chromatography, the resulting compound of formula (VII) can be obtained in at least 85% yield. Alternatively, the compound of formula (VII) can be isolated as the corresponding H$_3$PO$_4$ salt with the concomitant removal of nonpolar and neutral impurities. The compound of formula (VII) can be hydrolyzed by treating with aqueous HCl, aqueous HOAc, or tetrabutylammonium fluoride (TBAF) in a suitable solvent (such as MeOH, EtOH, THF, acetone, or MeCN) to provide pure abiraterone of formula (I) with higher than 99% purity.

Similarly, abiraterone of formula (I) with higher than 99% purity can be obtained by hydrolyzing a compound of formula (VII), or an $H_3PO_4$ salt thereof, using the aqueous acids with or without a suitable cosolvent (such as MeOH, EtOH, THF, acetone, or MeCN). See FIG. 14, Scheme 10.

In some embodiments, the vinyl triflate of formula (IV) can be subjected to deprotection prior to the following Suzuki coupling step (FIG. 14, Scheme 10). Deprotection of the hydroxy group can be achieved by treating the vinyl triflate of formula (IV) with aqueous HCl, aqueous HOAc, or TBAF in a suitable solvent such as MeOH, EtOH, THF, acetone and MeCN. The resulting vinyl triflate of formula (V) can be isolated in over 80% yield with higher than 95% purity. When the vinyl triflate of formula (V) is employed in the Suzuki coupling step, abiraterone of formula (I) can be obtained in over 89% yield with higher than 97% purity.

Figure 15:
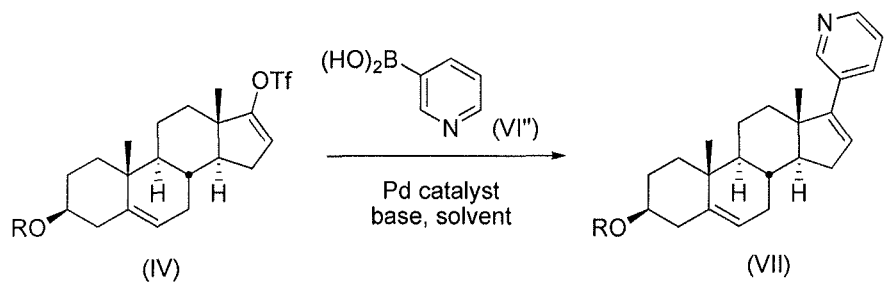
FIG. 15 provides Scheme 11 illustrating Suzuki coupling of vinyl triflate of Formula (IV) with 3-Pyridylboronic acid of formula (VI").

In some embodiments, 3-pyridylboronic acid can react in a manner similar to diethyl(3-pyridyl)borane. When the vinyl triflate of formula (IV) and 3-pyridylboronic acid of formula (VI") are employed in the Suzuki coupling step, the resulting compound of formula (VII) can be isolated in at least 67% yield (FIG. 15, Scheme 11).

Figure 16:
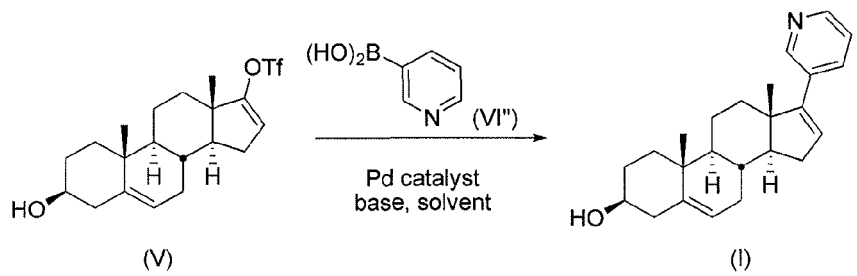
FIG. 16 provides Scheme 12 illustrating Suzuki coupling of vinyl triflate of Formula (V) with 3-Pyridylboronic acid of formula (VI").

In a very straightforward manner, abiraterone of formula (I) can be generated from coupling of vinyl triflate of formula (V) and 3-pyridylboronic acid of formula (VI") (FIG. 16, Scheme 12). The resulting abiraterone of formula (I) can be isolated in over 50% yield.

Figure 17:
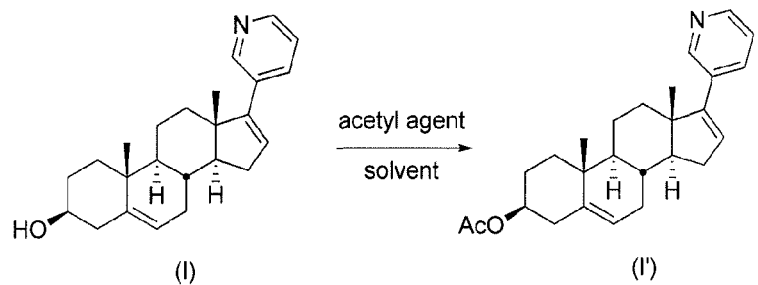
FIG. 17 provides Scheme 13 illustrating formation of Abiraterone Acetate of formula (I').

In some embodiments, abiraterone of formula (I) is converted to abiraterone acetate of the formula (I'). Abiraterone of formula (I) is reacted with a suitable acylating reagent such as $Ac_2O$ or acetyl chloride in the presence of a suitable base which can be selected from DMAP, $Et_3N$, DIPEA, metal carbonate such as alkaline metal carbonate (such as potassium carbonate ($K_2CO_3$)), metal bicarbonate such as an alkali metal bicarbonate (such as sodium bicarbonate ($NaHCO_3$)) or pyridine in the reaction solvent which includes acetone, tetrahydrofuran (THF) or dichloromethane (DCM) (see FIG. 17, Scheme 13).

In another aspect, the invention provides a process for recrystallization of abiraterone acetate. The process comprises:
a) providing a solution of abiraterone acetate in an organic solvent, for example n-hexane, n-heptane, cyclohexane, acetone, acetonitrile (MeCN), dimethylsulfoxide (DMSO), methanol, ethanol or combinations thereof, with or without an addition of water;
b) heating the solution; and
c) isolating and drying the crystalline form of abiraterone acetate.

The resulting abiraterone acetate can be isolated in at least 95% yield with higher than 99.5% purity containing less than 0.10% of any single impurity. In some embodiments, the isolated crystalline abiraterone acetate is characterized by an X-ray powder diffraction (XRPD) pattern as shown is FIG. 1. In some embodiments, the isolated crystalline abiraterone acetate is characterized by an X-ray powder diffraction (XRPD) having peaks at 5.8°, 12.1°, 14.8°, 15.1°, 15.9°, 18.4°, 18.9°, 21.7°, 22.4°, and 23.0° 2θ (±0.2). Each of the noted peaks has a relative intensity of about 20% or more as the peak at 5.8° is 100%. In some embodiments, the isolated crystalline abiraterone acetate is characterized by an X-ray powder diffraction (XRPD) having three or more peaks selected from peaks at 5.8°, 12.1°, 14.8°, 15.1°, 15.9°, 18.4°, 18.9°, 21.7°, 22.4°, and 23.0° 2θ (±0.2). In some embodiments, the isolated crystalline abiraterone acetate is characterized by an X-ray powder diffraction (XRPD) having six or more peaks selected from peaks at 5.8°, 12.1°, 14.8°, 15.1°, 15.9°, 18.4°, 18.9°, 21.7°, 22.4°, and 23.0° 2θ (±0.2).

The following examples are illustrative of certain embodiments of the invention and should not be considered as limiting in any way.

IV. Examples

Figure 18:
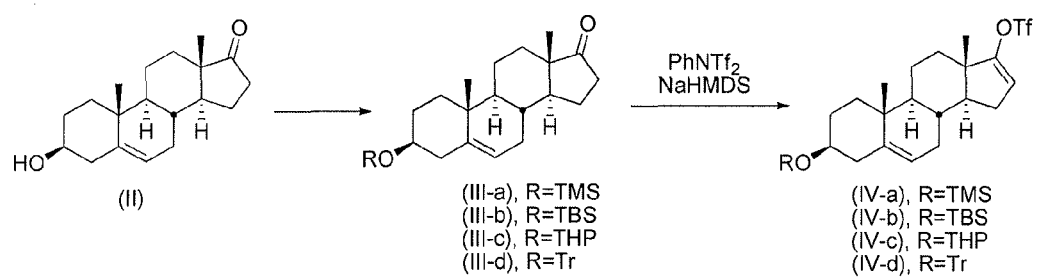
FIG. 18 provides the synthesis scheme for compounds of formula (III-a to III-d and IV-a to IV-d).

Formation of Vinyl Triflates of Formula (IV-a to IV-d) (See FIG. 18)

Example 1

Synthesis of Compound of Formula (III-a)

Prasterone of formula (II) (30 g, 104.2 mmole), imidazole (21.2 g, 312.6 mmole), and DCM (150 mL) were added to a suitable flask at 20-30° C. The mixture was stirred at 20-30° C. for about 5 min achieving a homogeneous solution. A mixture containing TMSCl (29.7 g, 234.5 mmole) and DCM (150 mL) was added at 20-30° C. The resulting mixture was stirred at 20-30° C. for 2 hours to complete the reaction. The mixture was filtered to remove the imidazole HCl salt, and the filtrate was concentrated at about 40° C. under reduced pressure to near dryness. MeCN (300 mL) was added to the concentrate, and the resulting mixture was distillated at about 40° C. under reduced pressure until the volume reached about 150 mL. The mixture was heated to about 78° C. achieving a homogeneous solution. After being cooled to 20-30° C., the mixture was filtered and the filtered cake was washed with MeCN (30 mL). The wet cake was dried at about 40° C. under reduced pressure to afford compound (III-a) (30.6 g) in 81.6% yield.

$^1$H-NMR (400 MHz, acetone-d6) δ 5.38 (d, J=5.2 Hz, 1H), 3.55-3.49 (m, 1H), 2.45-2.38 (m, 1H), 2.26-1.51 (m, 14H), 1.37-1.33 (m, 2H), 1.29-1.02 (m, 2H), 1.06 (s, 3H), 0.88 (s, 3H), 0.11 (s, 9H).

Example 2

Synthesis of Compound of Formula (IV-a)

Compound (III-a) (20 g, 55.6 mmole), $PhNTf_2$ (25.8 g, 72.3 mmole), and THF (100 mL) were added to a suitable flask at 20-30° C. The mixture was cooled to 0-10° C. NaHMDS (2M in THF, 41.7 mL, 83.4 mmole) was slowly added at 0-10° C. for 1 hour. After the reaction was completed, toluene (100 mL) and water (120 mL) were added to the mixture and the mixture was stirred at 20-30° C. for about 5 min. The organic portion was separated after phase separation, and was successively washed with 1N $HCl_{(aq)}$ (120 mL), 8% $NaHCO_{3(aq)}$ (120 mL), and water (120 mL). The resulting separated organic portion was concentrated at about 40° C. under reduced pressure to near dryness. The concentrate was subjected to flash column chromatography (eluent: EtOAc/n-heptane=1/50), and the purified compound of formula (IV-a) (24.7 g) was afforded in 90.3% yield.

$^1$H-NMR (400 MHz, CDCl$_3$) δ 5.60 (d, J=1.6 Hz, 1H), 5.36 (d, J=5.2 Hz, 1H), 3.56-3.47 (m, 1H), 2.32-2.20 (m, 3H), 2.07-2.00 (m, 2H), 1.18-1.59 (m, 10H), 1.15-1.04 (1.04 (s, 3H), 0.89 (s, 3H), 0.11 (s, 9H).

Example 3

Synthesis of Compound of Formula (III-b)

Prasterone of formula (II) (30 g, 104.2 mmole), imidazole (21.2 g, 312.6 mmole), DMAP (1.27 g, 10.4 mmole), and DCM (300 mL) were added to a suitable flask at 20-30° C. After TBSCl (31.3 g, 208.4 mmole) was added at 20-30° C., the mixture was heated to 30-40° C. and stirred for 2 hours completing the reaction. Water (150 mL) was added, and the mixture was stirred at 20-30° C. for about 5 min. After phase separation, the separated organic portion was concentrated at about 40° C. under reduced pressure to near dryness. Acetone (200 mL) was added to the concentrate, and the mixture was heated at 50-55° C. achieving a homogeneous solution. Water (400 mL) was added at 50-55° C., and the resulting mixture was stirred at this temperature for 30 min. After being cooled to 0-10° C., the mixture was filtered and the filtered cake was washed with a mixture of acetone and water (1/2, 40 mL). The wet cake was dried at about 40° C. under reduced pressure to afford compound (III-b) (40.7 g) in 97.2% yield.

$^1$H-NMR (400 MHz, CDCl$_3$) δ 5.37 (dd, J=3.6, 1.6 Hz, 1H), 3.54-3.48 (m, 1H), 2.52-2.45 (m, 1H), 2.13-1.40 (m, 14H), 1.30-1.29 (m, 2H), 1.15-1.05 (m, 2H), 1.05 (s, 3H), 0.91 (s, 3H), 0.91 (s, 9H), 0.08 (s, 6H).

Example 4

Synthesis of Compound of Formula (IV-b)

Compound (III-b) (6.9 g, 17.2 mmole), PhNTf$_2$ (12.2 g, 34.4 mmole), and THF (34.5 mL) were added to a suitable flask at 20-30° C. The mixture was cooled to 0-10° C. NaHMDS (1M in THF, 30.8 mL, 31.0 mmole) was slowly added at 0-10° C. for 1 hour. After the reaction was completed, the mixture was combined with toluene (70 mL) and water (100 mL). The resulting mixture was stirred at 20-30° C. for about 5 min. The organic portion was separated after phase separation. The organic portion was successively washed with 1N HCl$_{(aq)}$ (100 mL), 8% NaHCO$_{3(aq)}$ (100 mL), and water (100 mL). The resulting separated organic portion was concentrated at about 40° C. under reduced pressure to near dryness. The concentrate was subjected to flash column chromatography (eluent: EtOAc/n-heptane=1/50) to provide compound (IV-b) (7.89 g) in 85.9% yield.

$^1$H-NMR (400 MHz, CDCl$_3$) δ 5.60 (dd, J=3.2, 1.6 Hz, 1H), 5.35 (m, 1H), 3.53-3.49 (m, 1H), 2.30-2.22 (m, 3H), 2.06-2.00 (m, 2H), 1.83-1.48 (m, 10H), 1.15-1.06 (m, 2H), 1.06 (s, 3H), 1.02 (s, 3H), 0.91 (s, 9H), 0.08 (s, 6H).

Example 5

Synthesis of Compound of Formula (III-c)

Prasterone of formula (II) (700 g, 2.43 mole), 3,4-dihydro-2H-pyran (305 g, 3.63 mole), pyridinium p-toluenesulfonate (60.7 g, 0.24 mole), and DCM (16 L) were added to a suitable flask at 20-30° C. The mixture was stirred at 20-30° C. for 16 hours to complete the reaction. Water (8 L) was added at 20-30° C., and the mixture was stirred at this temperature for about 5 min. After phase separation, the separated organic portion was concentrated at 40-45° C. under reduced pressure until the volume reached about 3.5 L. Acetone (14 L) was added and the mixture was concentrated at 40-45° C. under reduced pressure until the volume reached about 7 L. Acetone (14 L) was added and the mixture was concentrated at 40-45° C. under reduced pressure until the volume reached about 7 L. Water (7 L) was added to the concentrate at 45-55° C., and the resulting mixture was stirred at this temperature for 1 hour. The mixture was cooled to 0-10° C. and stirred for 1 hour. The mixture was filtered and the filtered cake was washed with a mixture of acetone and water (1/1, 1.6 L). The wet cake was dried at about 40° C. under reduced pressure to afford compound (III-c) (873 g) in 96.6% yield.

$^1$H-NMR (400 MHz, CDCl$_3$) δ 5.37 (dd, J=11.6, 6.0 Hz, 1H), 4.71 (dd, J=4.8, 2.4 Hz, 1H), 3.91-3.89 (m, 1H), 3.54-3.49 (m, 2H), 3.37-2.46 (m, 2H), 2.20-1.52 (m, 20H), 1.28-1.27 (m, 1H), 1.09-0.99 (m, 2H), 0.99 (s, 3H), 0.88 (s, 3H).

Example 6

Synthesis of Compound of Formula (IV-c)

Compound (III-c) (36 g, 96.8 mmole), PhNTf$_2$ (60.5 g, 169.4 mmole), and THF (180 mL) were added to a suitable flask at 20-30° C. The mixture was cooled to 0-10° C. NaHMDS (1M in THF, 145.2 mL, 145.2 mmole) was slowly added at 0-10° C. for 1 hour. After the reaction was completed, the mixture was combined with toluene (180 mL) and water (540 mL). The resulting mixture was stirred at 20-30° C. for about 5 min. The organic portion was separated after phase separation. The organic portion was successively washed with 1N HCl$_{(aq)}$ (540 mL), 8% NaHCO$_3$ $_{(aq)}$ (540 mL), and water (540 mL). The resulting separated organic portion was concentrated at about 40° C. under reduced pressure to near dryness. The concentrate was subjected to flash column chromatography (eluent: EtOAc/n-heptane=1/30) and gave purified compound (IV-c) (40.9 g) in 83.8% yield.

$^1$H-NMR (400 MHz, CDCl$_3$) δ 5.59 (dd, J=3.2, 1.6 Hz, 1H), 5.37 (m, 1H), 4.74-4.72 (m, 1H), 3.94-3.92 (m, 1H), 3.56-3.50 (m, 2H), 2.40-2.39 (m, 1H), 2.30-2.22 (m, 1H), 2.05-1.50 (m, 19H), 1.10-1.06 (m, 2H), 1.06 (s, 3H), 1.01 (s, 3H).

Example 7

Synthesis of Compound of Formula (III-d)

Prasterone of formula (II) (10 g, 34.7 mmole), TrCl (17.4 g, 62.5 mmole), DMAP (0.42 g, 3.5 mmol), and pyridine (100 mL) were added to suitable flask at 20-30° C. The mixture was heated to 110° C. and stirred for 16 hours completing the reaction. DCM (500 mL) and water (300 mL) were added after the mixture was cooled to 20-30° C. The mixture was stirred at 20-30° C. for about 5 min. The separated organic portion was reserved after phase separation. To the separated aqueous portion was added DCM (200 mL) at 20-30° C., and the mixture was stirred at this temperature for about 5 min. The separated organic portion was reserved after phase separation. The two organic portions were combined and concentrated at about 40° C. under reduced pressure to near dryness. The concentrate was subjected to flash column chromatography (eluent: EtOAc/n-heptane=1/10) and gave purified compound (III-d) (12.5 g) in 67.9% yield.

$^1$H-NMR (400 MHz, CDCl$_3$) δ 7.56-7.53 (m, 6H), 7.33-7.25 (m, 9H), 4.94 (d, J=5.2, Hz, 1H), 3.41-3.36 (m, 1H), 2.49-2.42 (m, 1H), 2.20-1.20 (m, 16H), 0.99 (s, 3H), 0.86 (s, 3H), 0.91-0.78 (m, 2H).

Example 8

Synthesis of Compound of Formula (IV-d)

Compound (III-d) (10.5 g, 19.8 mmole), PhNTf$_2$ (14.1 g, 39.6 mmole), and THF (55 mL) were added to a suitable flask at 20-30° C. The mixture was cooled to 0-10° C. NaHMDS (1M in THF, 35.6 mL, 35.6 mmol) was slowly added at 0-10° C. for 1 hour. After the reaction was completed, the mixture was combined with toluene (50 mL) and water (160 mL). The separated organic portion was reserved after phase separation. To the separated aqueous portion was added toluene (50 mL) at 20-30° C., and the mixture was stirred at this temperature for about 5 min. The separated organic portion was reserved after phase separation. The two organic portions were combined and concentrated at about 40° C. under reduced pressure to near dryness. The concentrate was subjected to flash column chromatography (eluent: EtOAc/n-heptane=1/50) and gave purified compound (IV-d) (9.4 g) in 71.7% yield.

$^1$H-NMR (400 MHz, CDCl$_3$) δ 7.56-7.53 (m, 6H), 7.33-7.25 (m, 9H), 5.57 (dd, J=3.2, 1.6 Hz, 1H), 4.91 (d, J=5.2 Hz, 1H), 3.38-3.37 (m, 1H), 2.23-2.15 (m, 2H), 2.01-1.94 (m, 2H), 1.87-1.34 (m, 11H), 1.03 (s, 3H), 0.99 (s, 3H), 0.99-0.81 (m, 2H).

Alternatively, NaHMDS can be replaced by other strong bases such as LiHMDS, KHMDS or LDA. Each base was added to a solution containing compound (III, 5 mmol) and PhNTf$_2$ (1/1.3, equiv/equiv) in THF (5 vol) at 0-10° C. for about 1 hour. The yields (over the steps from the compound (III-a to III-d)) of the resulting compounds (IV) were obtained using other strong bases are also listed in Table 1, for example, KHMDS provided the yield in a range of 81.6%~93.4%; LiHMDS provided the yield in a range of 80.8%~93.7%; LDA provided the yield in a range of 56.9%~71.0%.

TABLE 1

Results of Vinyl Triflate Compounds (IV) Formation

| Compound (III) | Base | Yield (%)[1] |
|---|---|---|
| a | LiHMDS | 93.7 |
| b | LiHMDS | 80.8 |
| c | LiHMDS | 84.9 |
| d | LiHMDS | 92.3 |
| a | KHMDS | 93.4 |
| b | KHMDS | 81.6 |
| c | KHMDS | 85.3 |
| d | KHMDS | 92.0 |
| a | LDA | 71.0 |
| b | LDA | 56.9 |
| c | LDA | 65.0 |
| d | LDA | 68.2 |

[1] The number is calculated based on HPLC solution assay

Figure 19:
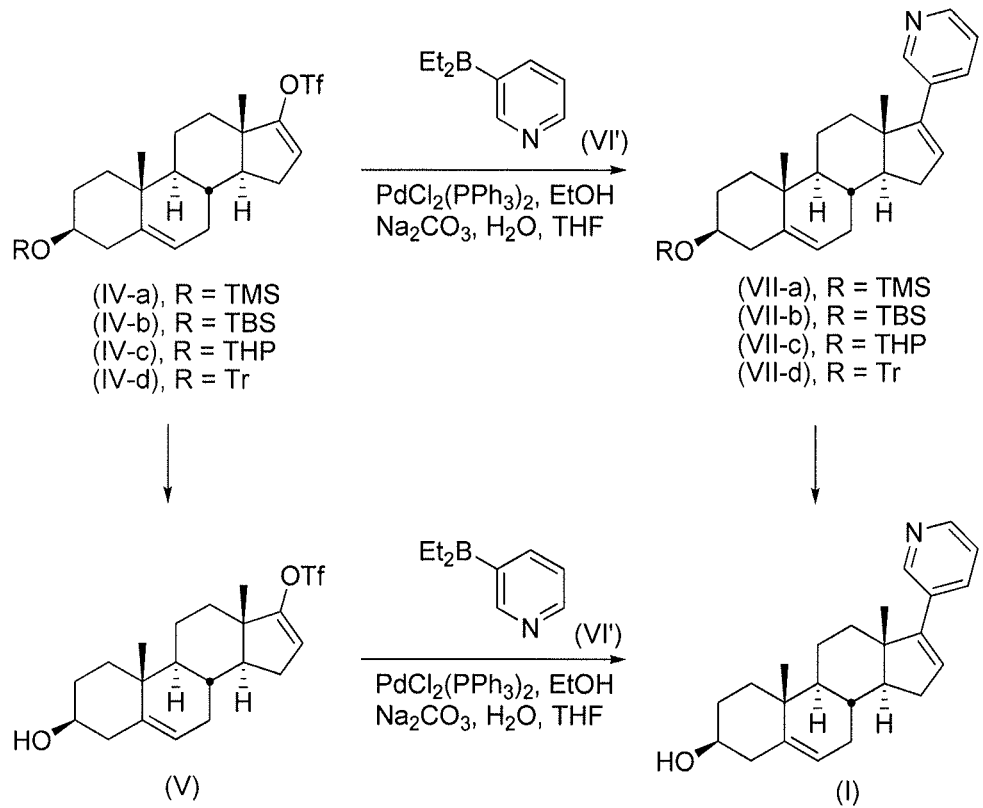
FIG. 19 provides another synthesis scheme for the formation of Abiraterone of Formula (I).

Synthesis of Abiraterone (I) (see FIG. 19)

Example 9

Synthesis of Compound of Formula (VII-a)

Compound (IV-a) (2.0 g, 4.1 mmole), diethyl(3-pyridyl)borane (0.6 g, 4.1 mmole), Na$_2$CO$_3$ (0.43 g, 4.1 mmole), PdCl$_2$(PPh$_3$)$_2$ (21 mg, 0.03 mmole), toluene (10 mL), THF (6 mL), EtOH (4 mL), and water (10 mL) were added to a suitable flask at 20-30° C. The mixture was heated to 70-75° C. for 0.5 hour. After the reaction was completed, the organic portion was separated after phase separation. The organic portion was washed with water (20 mL). The resulting separated organic portion was concentrated at about 40° C. under reduced pressure to near dryness. The concentrate was subjected to flash column chromatography (eluent: EtOAc/n-Heptane=1/7), and purified compound (VII-a) (1.48 g) was afforded in 86.2% yield.

$^1$H-NMR (400 MHz, CDCl$_3$) δ 8.64 (d, J=1.6 Hz, 1H), 8.48 (dd, J=4.8, 1.6 Hz, 1H), 7.67 (ddd, 1H), 7.26-7.22 (m, 1H), 6.02 (dd, J=3.2, 1.6 Hz, 1H), 5.39 (dd, J=5.2, 3.2 Hz, 1H), 3.56-3.48 (m, 1H), 2.37-2.20 (m, 3H), 2.12-2.04 (m, 3H), 1.86-1.45 (m, 9H), 1.16-1.09 (m, 2H), 1.08 (s, 3H), 1.07 (s, 3H), 0.14 (s, 9H).

Example 10

Synthesis of Compound of Formula (VII-b)

Compound (IV-b) (13.3 g, 24.8 mmole), diethyl(3-pyridyl)borane (5.5 g, 37.4 mmole), Na$_2$CO$_3$ (8.5 g, 80.2 mmole), PdCl$_2$(PPh$_3$)$_2$ (350 mg, 0.5 mmole), toluene (67 mL), THF (40 mL), EtOH (20 mL), and water (100 mL) were added to a suitable flask at 20-30° C. The resulting mixture was heated to 70-75° C. for 1 hour. After the reaction was completed, the organic portion was separated after phase separation. The organic portion was washed with water (100 mL), separated, and concentrated at about 40° C. under reduced pressure to near dryness. The concentrate was subjected to flash column chromatography (eluent: EtOAc/n-Heptane=1/6), and purified compound (VII-b) (9.38 g) was afforded in 81.7% yield.

$^1$H-NMR (400 MHz, CDCl$_3$) 8.64 (d, J=1.6 Hz, 1H), 8.48 (dd, J=4.8, 1.6 Hz, 1H), 7.67 (ddd, 1H), 7.26-7.23 (m, 1H), 6.02 (dd, J=3.2, 1.6 Hz, 1H), 5.38 (dd, J=5.6, 2.0 Hz, 1H), 3.56-3.48 (m, 1H), 2.35-2.20 (m, 3H), 2.15-2.05 (m, 3H), 1.88-1.47 (m, 9H), 1.14-1.09 (m, 2H), 1.08 (s, 3H), 1.07 (s, 3H), 0.92 (s, 9H), 0.09 (s, 6H).

Example 11

Synthesis of Compound of Formula (VII-c)

Compound (IV-c) (2.0 g, 4.0 mmole), diethyl(3-pyridyl)borane (0.59 g, 4.0 mmole), Na$_2$CO$_3$ (0.25 g, 2.4 mmole), PdCl$_2$(PPh$_3$)$_2$ (14 mg, 0.02 mmole), toluene (10 mL), THF (6 mL), EtOH (4 mL), and water (10 mL) were added to a suitable flask at 20-30° C. The mixture was heated to 70-75° C. for 2 hours. After the reaction was completed, the organic portion was separated after phase separation. The organic portion was washed with water (20 mL). The resulting separated organic portion was concentrated at about 40° C. under reduced pressure to near dryness. The concentrate was subjected to flash column chromatography (eluent: EtOAc/n-Heptane=1/4), and purified compound (VII-c) (1.48 g) was afforded in 85.5% yield.

$^1$H-NMR (400 MHz, CDCl$_3$) δ 8.62 (d, J 1.6 Hz, 1H), 8.46 (dd, J=4.8, 1.6 Hz, 1H), 7.65 (ddd, 1H), 7.29-7.20 (m, 1H), 6.00 (dd, J=3.2, 2.0 Hz, 1H), 5.39 (dd, J=5.6, 2.0 Hz, 1H), 4.74-4.72 (m, 1H), 3.93-3.92 (m, 1H), 3.55-3.51 (m, 2H), 2.40-2.39 (m, 2H), 2.26-2.24 (m, 2H), 2.06-2.04 (m, 3H), 1.88-1.49 (m, 14H), 1.10-1.05 (m, 2H), 1.08 (s, 3H), 1.05 (s, 3H).

Example 12

Synthesis of Compound of Formula (VII-d)

Compound (IV-d) (12.5 g, 18.8 mmole), diethyl(3-pyridyl)borane (4.1 g, 28.2 mmole), Na$_2$CO$_3$ (8.5 g, 80.2 mmole), PdCl$_2$(PPh$_3$)$_2$ (130 mg, 0.19 mmole), toluene (63 mL), THF (38 mL), EtOH (20 mL), and water (100 mL) were added to a suitable flask at 20-30° C. The mixture was heated to 70-75° C. for 0.5 hour. After the reaction was completed, the organic portion was separated after phase separation. The organic portion was washed with water (100 mL). The resulting separated organic portion was concentrated at about 40° C. under reduced pressure to near dryness. The concentrate was subjected to flash column chromatography (eluent: EtOAc/n-Heptane=1/6), and purified compound (VII-d) (9.45 g) was afforded in 85.0% yield.

$^1$H-NMR (400 MHz, CDCl$_3$) δ 8.62 (d, J=1.6 Hz, 1H), 8.47 (dd, J=4.8, 1.6 Hz, 1H), 7.71 (ddd, 1H), 7.56-7.54 (m, 6H), 7.33-7.23 (m, 10H), 6.02 (dd, J=2.8, 1.6 Hz, 1H), 4.95 (dd, J=4.8, 2.0 Hz, 1H), 3.40-3.37 (m, 1H), 2.89-2.11 (m, 2H), 2.10-1.94 (m, 2H), 1.71-1.27 (m, 11H), 1.03 (s, 3H), 1.02 (s, 3H), 0.98-0.81 (m, 2H).

Example 13

Synthesis of Compound of Formula (V)

Compound of Formula (IV-a)→Compound of Formula (V)
Compound (IV-a) (17.0 g, 34.6 mmole), THF (90 mL), and n-heptane (40 mL) were added to a suitable flask at 20-30° C. The mixture was stirred at 20-30° C. for about 5 min achieving a homogenous solution. 2N HCl$_{(aq)}$ (35 mL) was added at 20-30° C., and the mixture was stirred at this temperature for 2 hours. After the reaction was completed, the organic portion was separated after phase separation. 4% NaHCO$_{3(aq)}$ (20 mL) was added at 20-30° C. adjusting pH at 8-9, and the mixture was stirred at this temperature for about 5 min. The resulting organic portion was concentrated at about 90-95° C. until the volume reached about 50 mL. n-Heptane (100 mL) was added to the mixture at 90-95° C., and the resulting mixture was cooled to 70-75° C. for 1 hour. The mixture was then cooled to 0-10° C. and stirred for 1 hour. The mixture was filtered and filtered cake was washed with n-heptane (20 mL). The wet cake was dried at about 60° C. under reduced pressure to afford compound (V) (12.3 g) in 84.8% yield.

Compound of Formula (IV-b)→Compound of Formula (V)
Compound (IV-b) (1.0 g, 1.9 mmole) and acetone (10 mL) were added to a suitable flask at 20-30° C. The mixture was added 12N HCl$_{(aq)}$ (0.2 mL) adjusting pH at 1-2 and stirred for 10 minutes. After reaction was completed, the mixture was combined with 4% NaHCO$_{3(aq)}$ (10 mL) adjusting pH to 7-8 and water (10 mL) at 20-30° C. The resulting mixture was cooled to 0-10° C. and stirred for 1 hour. The mixture was filtered and filtered cake was washed with water (2 mL). The wet cake was dried at about 40° C. under reduced pressure to afford compound (V) (0.72 g) in 90.2% yield.

Compound of Formula (IV-c)→Compound of Formula (V)
Compound (IV-c) (1.0 g, 2.0 mmole), 2N HCl$_{(aq)}$ (1.0 mL) and MeOH (10 mL) were added to a suitable flask at 20-30° C. The mixture was heated to 60-65° C. and stirred for 30 minutes. After reaction was completed, the mixture was cooled to 20-30° C. and 2% NaHCO$_{3(aq)}$ (20 mL) was added adjusting the pH to 7-8. The resulting mixture was cooled to 0-10° C. and stirred for 1 hour. The mixture was filtered and filtered cake was washed with water (2 mL). The wet cake was dried at about 60° C. under reduced pressure to afford compound of formula (V) (0.81 g) in 96.4% yield.

Compound of Formula (IV-d)→Compound of Formula (V)
Compound (IV-d) (1.0 g, 1.5 mmole) and acetone (10 mL) were added to a suitable flask at 20-30° C. To the mixture was added 12N HCl$_{(aq)}$ (0.2 mL) adjusting pH to 1-2 and stirred for 1.5 hours. After the reaction was completed, the mixture was combined with 2% NaHCO$_{3(aq)}$ (20 mL) adjusting the pH to 7-8 at 20-30° C. The resulting mixture was cooled to 0-10° C. and stirred for 1 hour. The mixture was filtered and filtered cake was washed with water (2 mL). The wet cake was dried at about 40° C. under reduced pressure to afford compound (V) (0.52 g) in 82.5% yield.

$^1$H-NMR (400 MHz, CDCl$_3$) δ 5.61 (dd, J=3.2, 1.6 Hz, 1H), 5.39 (dd, J=3.6, 2.4 Hz, 1H), 3.59-3.52 (m, 1H), 2.37-2.23 (m, 3H), 2.07-2.00 (m, 2H), 1.93-1.44 (m, 11H), 1.18-1.10 (m, 2H), 1.06 (s, 3H), 1.02 (s, 3H).

Example 14

Synthesis of Abiraterone of Formula (I)

Compound of Formula (VII-a)→Abiraterone of Formula (I)
Compound (VII-a) (0.5 g, 1.2 mmole) and MeOH (5 mL) were added to a suitable flask at 20-30° C. To the mixture was added 2N HCl$_{(aq)}$ (0.85 mL) adjusting the pH to 1-2 with stirring for 1.5 hours. After the reaction was completed, the mixture was combined with 4% NaHCO$_{3(aq)}$ (2.8 mL) adjusting the pH to 7-8, and water (5 mL) was added at 20-30° C. The resulting mixture was cooled to 0-10° C. and stirred for 1 hour. The mixture was filtered and filtered cake was washed with water (2 mL). The wet cake was dried at about 40° C. under reduced pressure to afford abiraterone (I) (0.4 g) in 96.6% yield.

Compound of Formula (VII-b)→Abiraterone of Formula (I)
Compound (VII-b) (1.0 g, 2.2 mmole), 12N HCl$_{(aq)}$ (0.22 mL), and MeOH (10 mL) were added to a suitable flask at 20-30° C. The mixture was stirred at 20-30° C. for 1 hour, achieving a homogeneous solution. After the reaction was completed, the mixture was added 17% Na$_2$CO$_{3(aq)}$ (10 mL) adjusting the pH to 11-12, and water (20 mL) was added at 20-30° C. The resulting mixture was cooled to 0-10° C. and stirred for 1 hour. The mixture was filtered and filtered cake was washed with water (4 mL). The wet cake was dried at about 40° C. under reduced pressure to afford abiraterone (I) (0.74 g) in 96.5% yield.

Compound of Formula (VII-c)→Abiraterone of Formula (I)
Compound (VII-c) (0.5 g, 1.2 mmole) and MeOH (5 mL) were added to a suitable flask at 20-30° C. To the mixture was added 2N HCl$_{(aq)}$ (0.82 mL) adjusting the pH to 1-2 and stirring was continued for 4 hours. After the reaction was completed, the mixture was combined with 4% NaHCO$_{3(aq)}$ (3.5 mL), adjusting the pH to 7-8, and water (5 mL) was added at 20-30° C. The resulting mixture was cooled to 0-10° C. and stirred for 1 hour. The mixture was filtered and filtered cake was washed with water (2 mL). The wet cake was dried at about 40° C. under reduced pressure to afford abiraterone (I) (0.38 g) in 94% yield.

Compound of Formula (VII-d)→Abiraterone of Formula (I)
Compound (VII-d) (1.0 g, 1.7 mmole), 12N HCl$_{(aq)}$ (0.22 mL), and MeOH (10 mL) were added to a suitable flask at 20-30° C. The mixture was stirred at 20-30° C. for 1 hour achieving a homogeneous solution. After the reaction was completed, the mixture was combined with 17% Na$_2$CO$_{3(aq)}$ (20 mL) adjusting the pH to 11-12, and water (20 mL) was added at 20-30° C. The resulting mixture was cooled to 0-10° C. and stirred for 1 hour. The mixture was filtered and filtered cake was washed with water (4 mL). The wet cake was dried at about 40° C. under reduced pressure to afford abiraterone (I) (0.57 g) in 96.1% yield.

Compound of Formula (V)→Abiraterone of Formula (I)
Compound (V) (1.68 g, 4.0 mmole), diethyl(3-pyridyl)borane (0.88 g, 6.0 mmole), Na$_2$CO$_3$ (0.43 g, 4.0 mmole), PdCl$_2$(PPh$_3$)$_2$ (28 mg, 0.04 mmole), THF (10 mL), and water (5 mL) were added to a suitable flask at 20-30° C. The mixture was heated to 70-75° C. for 0.5 hour. After the reaction was completed, the organic portion was separated after phase separation. The organic portion was washed with water (100 mL). The resulting separated organic portion was concentrated at about 65-70° C. till volume reached about 8 mL EtOH (10 mL) and water (10 mL) were added to the concentrate at 65-70° C. The resulting mixture was stirred at 65-70° C. for 1 hour. The mixture was cooled to 20-30° C. and stirred for 1 hour. The mixture was filtered and filtered cake was washed with water (10 mL). The wet cake was dried at about 40° C. under reduced pressure to afford abiraterone of formula (I) (1.24 g) in 88.8% yield.

$^1$H-NMR (400 MHz, CDCl$_3$) δ 8.64 (d, J=1.6 Hz, 1H), 8.48 (dd, J=4.8, 1.6 Hz, 1H), 7.67 (ddd, 1H), 7.26-7.22 (m, 1H), 6.02 (dd, J=3.2, 1.6 Hz, 1H), 5.42 (dd, J=5.2, 2.4 Hz, 1H), 3.60-3.53 (m, 1H), 2.38-2.25 (m, 3H), 2.13-2.04 (m, 2H), 1.93-1.45 (m, 10H), 1.18-1.10 (m, 2H), 1.09 (s, 3H), 1.07 (s, 3H).

Example 15

Figure 20:
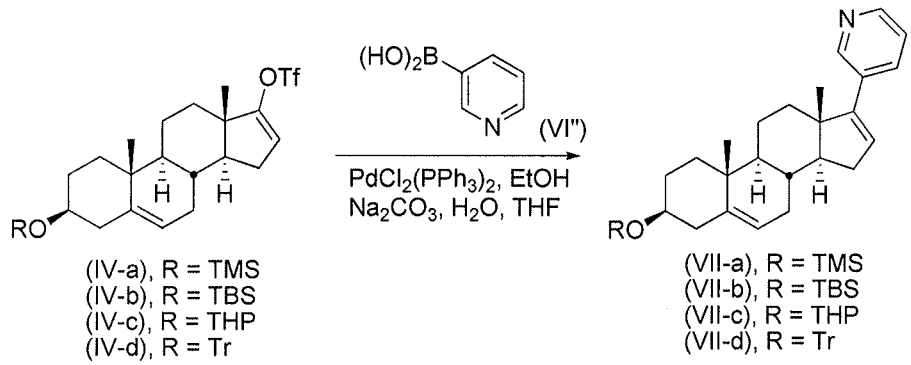
FIG. 20 provides a synthesis scheme for Suzuki coupling of vinyl triflates of formula (IV-a-d) with 3-Pyridylboronic acid of Formula (VI").

Synthesis of Compound of Formula (VII-a) (See FIG. 20)

Compound (IV-a) (2.02 g, 4.1 mmole), 3-pyridineboronic acid (0.77 g, 6.1 mmole), Na$_2$CO$_3$ (1.72 g, 16.2 mmole), PdCl$_2$(PPh$_3$)$_2$ (56 mg, 0.08 mmole), toluene (10 mL), THF (6 mL), EtOH (4 mL) and water (10 mL) were added to a suitable flask at 20-30° C. The mixture was heated to 70-75° C. for 1.5 hours completing the reaction. After the mixture was cooled to 20-30° C., the stirring was stopped to affect phase separation. The separated organic portion was saved, and the separated aqueous portion was discarded. The reserved organic portion was washed with water (20 mL). The resulting separated organic portion was concentrated at about 60° C. under reduced pressure to near dryness. The concentrate was subjected to flash column chromatography (eluent: toluene/n-heptane=1/5, containing 1% of Et$_3$N). The purified compound (VII-a) (1.34 g) was afforded in 77.6% yield.

Example 16

Synthesis of Compound of Formula (VII-b)

Compound (IV-b) (2.0 g, 3.74 mmole), 3-pyridineboronic acid (0.69 g, 5.61 mmole), Na$_2$CO$_3$ (0.4 g, 3.74 mmole), PdCl$_2$(PPh$_3$)$_2$ (165 mg, 0.23 mmole), THF (12 mL) and water (6 mL) were added to a suitable flask at 20-30° C. The mixture was heated to 60-65° C. for 6 hours completing the reaction. Toluene (10 mL) was added after the mixture was cooled to 20-30° C. The stirring was stopped to affect phase separation. The separated organic portion was saved, and the separated aqueous portion was discarded. The reserved organic portion was washed with water (20 mL). The resulting separated organic portion was concentrated at about 60° C. under reduced pressure to near dryness. The concentrate was subjected to flash column chromatography (eluent: toluene/n-heptane=1/4). The purified compound (VII-b) (1.17 g) was afforded in 67.5% yield.

Example 17

Synthesis of Compound of Formula (VII-c)

Compound (IV-c) (2.14 g, 4.0 mmole), 3-pyridineboronic acid (0.63 g, 5.0 mmole), Na$_2$CO$_3$ (0.43 g, 4.0 mmole), PdCl$_2$(PPh$_3$)$_2$ (56 mg, 0.08 mmole), toluene (10 mL), THF (6 mL), EtOH (4 mL) and water (10 mL) were added to a suitable flask at 20-30° C. The mixture was heated to 70-75° C. for 2.5 hours completing the reaction. After the mixture was cooled to 20-30° C., the stirring was stopped to affect phase separation. The separated organic portion was saved, and the separated aqueous portion was discarded. The reserved organic portion was washed with water (20 mL). The resulting separated organic portion was concentrated at about 60° C. under reduced pressure to near dryness. The concentrate was subjected to flash column chromatography (eluent: EtOAc/toluene=1/4, containing 1% of Et$_3$N). The purified compound (VII-c) (1.26 g) was afforded in 72.7% yield.

Example 18

Synthesis of Compound of Formula (VII-d)

Compound (IV-d) (2.0 g, 3.0 mmole), 3-pyridineboronic acid (0.55 g, 4.5 mmole), Na$_2$CO$_3$ (0.32 g, 3.0 mmole), PdCl$_2$(PPh$_3$)$_2$ (126 mg, 0.18 mmole), THF (12 mL) and water (6 mL) were added to a suitable flask at 20-30° C. The mixture was heated to 60-65° C. for 6 hours completing the reaction. Toluene (10 mL) was added after the mixture was cooled to 20-30° C. The stirring was stopped to affect phase separation. The separated organic portion was saved, and the separated aqueous portion was discarded. The reserved organic portion was washed with water (20 mL). The resulting separated organic portion was concentrated at about 60° C. under reduced pressure to near dryness. The concentrate was subjected to flash column chromatography (eluent: EtOAc/n-heptane=1/6). The purified compound (VII-d) (1.41 g) was afforded in 80.2% yield.

Example 19

Figure 21:
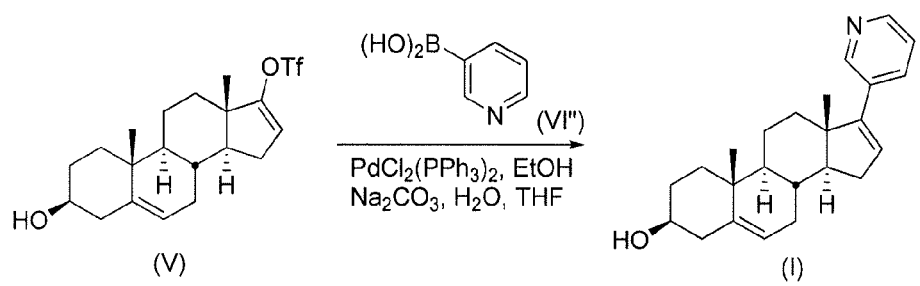
FIG. 21 provides a synthesis scheme for Suzuki coupling of vinyl triflate of formula (V) with 3-Pyridylboronic acid of Formula (VI").

Synthesis of Abiraterone of Formula (I) (See FIG. 21)

Compound (V) (1.68 g, 4.0 mmole), 3-pyridineboronic acid (0.74 g, 6.0 mmole), Na$_2$CO$_3$ (0.43 g, 4.0 mmole), PdCl$_2$(PPh$_3$)$_2$ (168 mg, 0.24 mmole), toluene (10 mL), THF (6 mL), EtOH (4 mL) and water (10 mL) were added to a suitable flask at 20-30° C. The mixture was heated to 70-75° C. for 2.5 hours completing the reaction. Most of the THF was removed by distillation under normal pressure. After toluene (20 mL) was added, the resulting mixture was cooled to 20-30° C. and stirred for 1 hour. The mixture was filtered and the filtered cake was washed with EtOH (5 mL). The purified abiraterone (I) (0.72 g) was afforded in 51.6% yield.

Example 20

Synthesis of Abiraterone Acetate of Formula (I')

Abiraterone (I) (7 g, 20 mmole), DMAP (122 mg, 1 mmole), Ac$_2$O (6.12 g, 60 mmole), and acetone (42 mL) were added to a suitable flask at 20-30° C. The mixture was heated to 55-65° C. and stirred for 1 hour. Water (14 mL) and abiraterone acetate seed (35 mg, 0.5 wt %) were added at 50-55° C. after the reaction was completed. The mixture was stirred at 50-55° C. for 1 hour. After water (35 mL) was added, the mixture was cooled to 0-5° C. and stirred for 1 hour. The mixture was filtered and filtered cake was washed with a mixture of acetone and water (1/1, 28 mL). The wet cake was dried at about 60° C. under reduced pressure to afford abiraterone acetate (I') (7.45 g) in 95.3% yield.

$^1$H-NMR (400 MHz, CDCl$_3$) δ 8.62 (d, J=1.6 Hz, 1H), 8.46 (dd, J=4.8, 1.6 Hz, 1H), 7.64 (m, 1H), 7.28-7.20 (m, 1H), 5.99 (dd, J=3.2, 2.0 Hz, 1H), 5.42 (dd, J=5.2, 2.4 Hz, 1H), 4.63-4.60 (m, 1H), 2.38-2.33 (m, 2H), 2.32-2.25 (m, 1H), 2.12-2.05 (m, 3H), 2.04 (s, 3H) 1.93-1.45 (m, 9H), 1.19-1.10 (m, 2H), 1.08 (s, 3H), 1.05 (s, 3H).

Example 21

Figure 22:
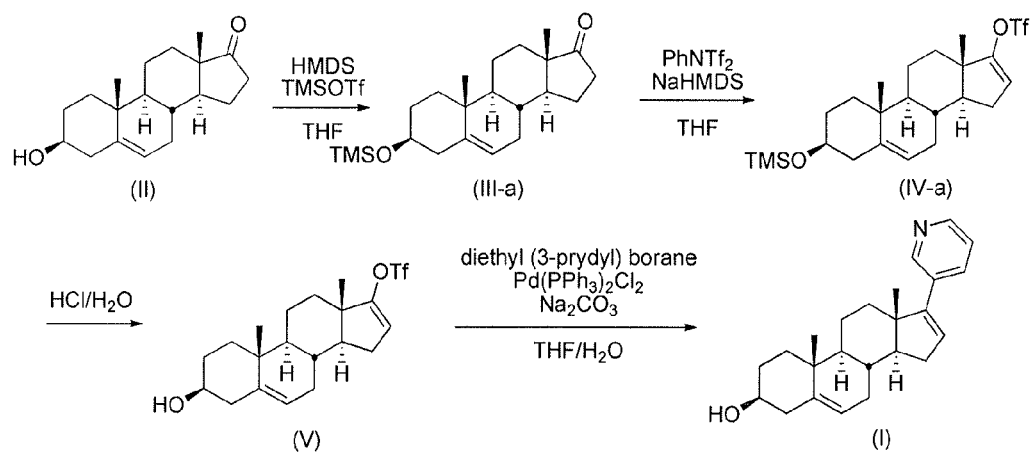
FIG. 22 provides a synthesis scheme for a one pot preparation of compound of formula (I).

Experimental of One Pot Preparation of Compound of Formula (I) (See FIG. 22)

Preparation of Compound of Formula (III-a)

Prasterone (II) (30 g, 104.2 mmole), HMDS (11.7 g, 72.9 mmole), and THF (210 mL) were added to a suitable flask at 20-30° C. A catalytic amount of TMSOTf (0.46 g, 2.08 mmole) was added at 20-30° C., and the mixture was stirred at this temperature for 20 min completing the reaction. The mixture was distilled at 45-55° C. to remove about 60 mL of solvent. After being cooled to 20-30° C., the resulting solution containing compound (III-a) was directly used in the next step.

Preparation of Compound (IV-a)

The solution containing compound (III-a) was added to a suitable flask followed by PhNTf$_2$ (48.4 g, 135.5 mmole) at 20-30° C. The mixture was cooled to 0-10° C., and NaHMDS (2M in THF, 78 mL, 156 mmole) was added at this temperature for 1 hour. Toluene (250 mL) was added and the resulting mixture was washed with water (480 mL). The separated organic solution was determined to contain 46.7 g (corresponded to 91.2%, over two steps from prasterone (II)) of compound (IV-a) by solution assay. The solution containing compound (IV-a) was directly used in the next step.

Preparation of Compound (V)

Partial of the solution containing compound (IV-a) (10.2 g, determined by solution assay) was added to a suitable flask at 20-30° C. HCl aqueous solution (0.1N, 92 mL) was added at 20-30° C., and the mixture was stirred at this temperature for 18 hours completing the reaction. The separated organic solution was sequentially washed with 8% NaHCO$_{3(aq)}$ (92 mL) and 10% NaCl$_{(aq)}$ (92 mL) at 20-30° C. The separated organic solution containing compound (V) was directly used in the next step.

Preparation of Abiraterone (I)

The solution containing compound (V) was added to a suitable flask followed by diethyl(3-pyridyl)borane (4.6 g, 31.2 mmole), Na$_2$CO$_3$ (2.2 g, 20.8 mmole) and PdCl$_2$(PPh$_3$)$_2$ (145 mg, 0.2 mmole) at 20-30° C. The mixture was heated to 70-75° C. for 40 min completing the reaction. The organic portion was separated at 60° C., and water (100 mL) was slowly added at this temperature. The mixture was cooled to 20-30° C. and stirred for 1 hour. The mixture was filtered and the filtered cake was washed with water (40 mL). The wet cake was dried at about 60° C. under reduced pressure to afford abiraterone (I) (5.38 g) in 74.0% yield (over four steps from prasterone (II)).

As reported in earlier syntheses, palladium (II) catalysts were used in abiraterone (I) formation. Undesired contamination of palladium is inevitably encountered. As described below, abiraterone (I) produced by the methods herein initially contained 165 ppm of palladium (Table 1, Entry 1). To reduce the level of palladium in abiraterone acetate (I') to not more than 10 ppm, a viable process for palladium content reduction is needed.

TABLE 1

Results of Palladium Removal[a]

| Entry | Scavenger | Residual Pd content (ppm) | Removal rate (%) |
|---|---|---|---|
| 1[b] | N/A | 165 | 95.0 |
| 2[c] | SiO$_2$ | 40.6 | 98.8 |
| 3[c] | PEP-21 | 2.0 | 99.9 |
| 4[d] | PEP-21 | 0.8 | 99.3 |
| 5[d] | PEP-27 | 0.6 | 99.5 |
| 6[c] | SiliaMetS Thiol | 15.4 | 99.6 |
| 7[c] | SiliaMetS Thiourea | 19.2 | 99.5 |
| 8[c] | SiliaMetS Cysteine | 33.3 | 99.0 |
| 9[c] | SiliaMetS DMT | 38.1 | 98.9 |
| 10[c] | SiliaMetS Triamine | 73.7 | 97.9 |
| 11[c] | SiliaMetS Imidazolel | 149.2 | 95.7 |
| 12[c] | SiliaMetS TAAcOH | 37.2 | 98.9 |
| 13[c] | SiliaMetS TAAcONa | 29.1 | 99.2 |

[a]General procedure: a mixture of crude abiraterone/toluene (1/30, w/v) was filtered at reflux temperature removing insoluble material. The scavenger (7.5 wt %) was added to the filtrate and the resulting mixture was stirred at reflux temperature for 1.5 hr followed by filtration. The resulting filtrate was cooled to 0-10° C. and filtered. Pd content in the purified abiraterone was measured by ICP-OES.
[b]Crude abiraterone (I) with Pd content at 3330 ppm was used.
[c]Crude abiraterone (I) with Pd content at 3463 ppm was used.
[d]Crude abiraterone (I) with Pd content at 118 ppm was used.

By subjecting crude abiraterone (I) to recrystallization from a suitable solvent (toluene or xylenes) in the presence of silica-based scavengers (see Entries 3-13), the purified abiraterone was obtained in 80-90% yield with greatly reduced Pd content. Structures of the scavengers are shown below. The scavengers used in Entries 3-5 are obtained from PhosphonicS, and the scavengers used in Entries 6-13 are obtained from Silicycle. PEP-21 and PEP-27 appeared to satisfactorily achieve residual palladium content at less than 10 ppm (Entries 3-5). In contrast, the purified abiraterone (I') contained 40.6 ppm of palladium when un-functionalized silica gel was used (Entry 2).

Structure of Scavengers

PEP-21

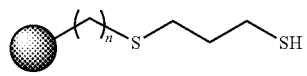

SiliaMetS Thiol/R51030B

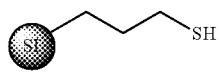

PEP-27

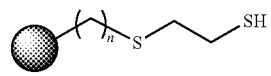

SiliaMetS Thiourea/R69530B

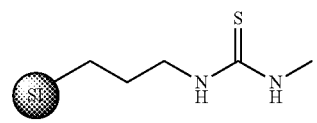

Structure of Scavengers

SiliaMetS Cysteine/R80530B

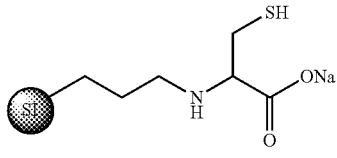

SiliaMetS DMT/R79030B

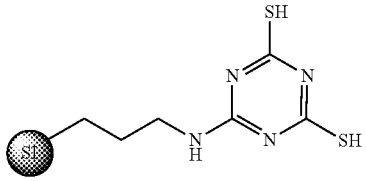

SiliaMetS Triamine/R48030B

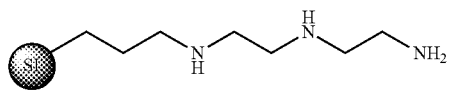

SiliaMetS Imidazolel/R69030B

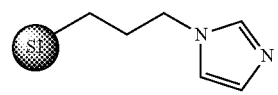

SiliaMetS TAAcOH/R69230B

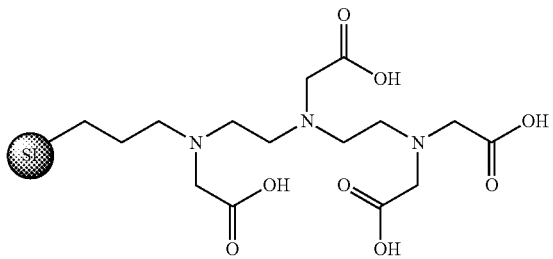

SiliaMetS TAAcONa/R79230B

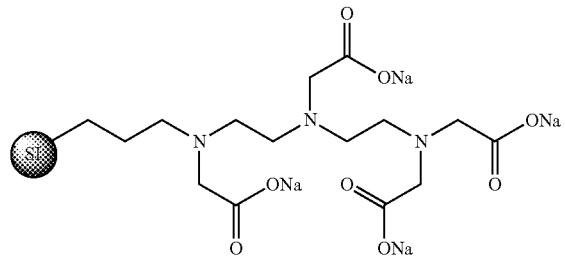

A Representative Procedure for Palladium Content Reduction in Abiraterone (I)

Crude abiraterone (40 g) and toluene (1200 mL) were added to a suitable flask at 20-40° C. The mixture was heated to reflux temperature and stirred for about 1 hr. The resulting mixture was filtered at about 100° C. removing insoluble material. Scavenger (PEP-21, 3 g,) was added. The mixture was heated at reflux temperature and stirred for about 1.5 hr. The resulting mixture was filtered at about 100° C. removing the scavenger. The solution was cooled to 0-10° C. and stirred for 1 hr. The mixture was filtered and the filtered cake was washed with toluene. The wet cake was dried at about 60° C. under reduced pressure affording purified abiraterone (35.7 g) in 89% yield containing 2 ppm of Pd.

Example 22

Crystallization from Acetone/Water

About 15 g of abiraterone acetate was dissolved in 120 mL of acetone at 50° C. The mixture was filtered while hot to a 500 mL reactor (jacket temperature 60° C., stirring rate 300 rpm) followed by rinse with 30 mL of acetone. Water (60 mL) was slowly added at about 60° C. reaching cloud point, and the mixture was stirred at this temperature for 5 min. After more water (90 mL) was added, the mixture was cooled to 20° C. and stirred for 1 hour. The mixture was filtered and the filtered cake was washed with a mixture of acetone and water (1/1, 45 mL). After being dried at 70° C. under reduced pressure for 18 hours, the resulting crystalline abiraterone acetate (14.6 g) was afforded in 96.5% yield.

XRPD pattern of the crystalline abiraterone acetate shows characteristic peaks at 5.8, 9.5, 10.7, 12.1, 12.6, 14.8, 15.1, 15.9, 16.5, 17.2, 17.6, 18.4, 18.9, 19.8, 21.7, 21.9, 22.4, 23.0, 23.5, 23.7, 24.3, 25.4, 26.0, 26.3, 26.8, 27.5, 27.9, 29.0, 29.5, 29.9, 30.5, 31.0, 31.2, 32.2, 33.1, 33.5, 33.8, 34.5, 34.8, 35.9, 36.8, 37.5, 38.4, 38.8, 39.4, and 39.8° 2-theta±0.2 (FIG. 1).

Example 23

Crystallization from Cyclohexane

Abiraterone acetate (30 g) was dissolved in cyclohexane (210 mL) at 20-40° C. The mixture was heated to 70-80° C. The solution was cooled and API seed (0.03 g) was added at 60-70° C. The resulting slurry is stirred at cloud point for 1 hr. The slurry was cooled to 10-25° C. and held for 1 hr. The mixture was filtered and the filtered cake was washed with cyclohexane at 10-25° C. The wet cake was dried at about 60° C. to get abiraterone acetate (24.9 g) in 89% yield.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

The invention claimed is:

1. A process for preparing abiraterone of formula (I):

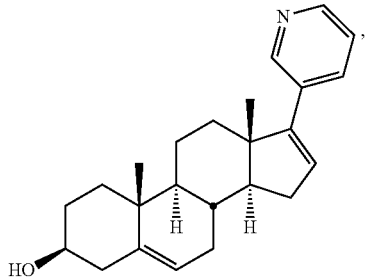

comprising:
(a) converting a compound of formula (II)

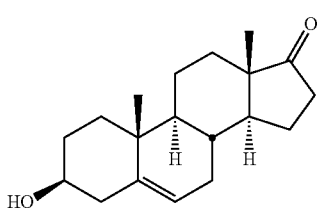

into a compound of formula (III)

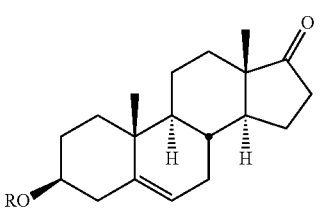

wherein R represents a hydroxy-protecting group;

(b) reacting the compound of formula (III) with a triflating agent followed by a strong base to give a compound of formula (IV)

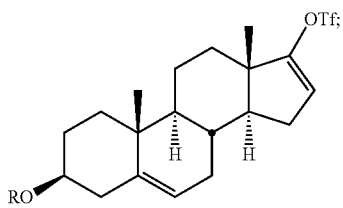

(c) deprotecting the compound of formula (IV) to give a compound of formula (V)

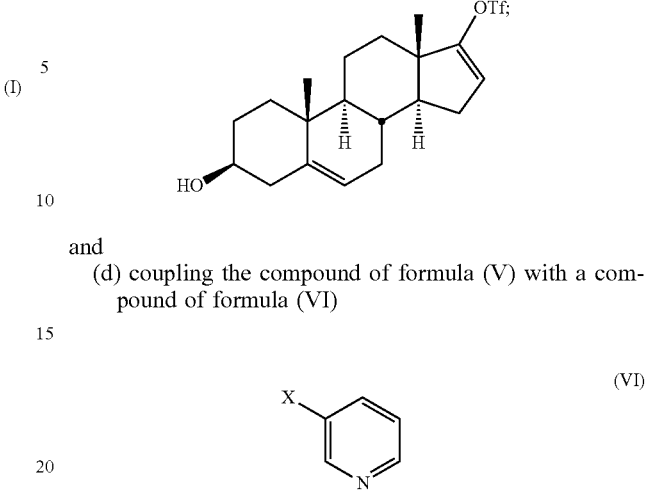

and
(d) coupling the compound of formula (V) with a compound of formula (VI)

wherein X is a boryl group, to provide abiraterone of formula (I).

2. The process according to claim 1, wherein the hydroxy-protecting group is selected from the group consisting of trimethylsilyl (TMS), tert-butyldimethylsilyl (TBS), tetrahydropyranyl (THP), triethylsilyl (TES), triisopropylsilyl (TIPS), dimethylphenylsilyl, diphenylmethylsilyl, tert-butyldiphenylsilyl (TBDPS) and triphenylmethyl (trityl, Tr).

3. The process of claim 2, wherein the hydroxy-protecting group is trimethylsilyl (TMS).

4. The process according to claim 1, wherein the triflating agent is selected from the group consisting of N-phenyl-bis (trifluoromethanesulfonimide), N-(5-chloro-2-pyridyl)triflimide or N-(2-pyridyl)triflimide.

5. The process of claim 4, wherein the triflating agent is N-phenyl-bis(trifluoromethanesulfonimide).

6. The process of claim 1, wherein the strong base is an amide based organometallic reagent selected from the group consisting of sodium hexamethyldisilazide (NaHMDS), potassium hexamethyldisilazide (KHMDS), lithium hexamethyldisilazide (LiHMDS) and lithium diisopropylamide (LDA).

7. The process of claim 6, wherein the amide based organometallic reagent is sodium hexamethyldisilazide (NaHMDS).

8. The process of claim 1, wherein X has the formula —$BY_2$, wherein Y is selected from alkyl, alkoxy or hydroxy group.

9. The process of claim 8, wherein Y is selected from the group consisting of ethyl and hydroxy.

10. The process of claim 1, wherein step (d) is performed in the presence of a palladium catalyst selected from the group consisting of bis(triphenylphosphine)palladium(II) dichloride ($PdCl_2(PPh_3)_2$), tetrakis(triphenylphosphine)palladium ($Pd(PPh_3)_4$), tris(dibenzylideneacetone)dipalladium ($Pd_2(dba)_3$), palladium acetate ($Pd(OAc)_2$), dichloro(1,2bis(diphenylphosphino)ethane)palladium(II) (PdCl2(dppe)2), [1,1'-bis(diphenylphosphino)ferrocene]palladium(II) dichloride dichloromethane ($PdCl_2(dppf)$ $CH_2Cl_2$), bis(benzonitrile)palladium (II) dichloride ($Pd(PhCN)_2Cl_2$) and bis(acetonitrile)palladium(II) dichloride ($Pd(CH_3CN)_2Cl_2$).

11. The process of claim 10, wherein abiraterone of formula (I) is purified by a scavenger selected from the group consisting silicon dioxide (SiO2), PEP-21, PEP-27, SiliaMetS Thiol, SiliaMetS Thiourea, SiliaMetS Cysteine, SiliaMetS DMT, SiliaMetS Triamine, SiliaMetS Imidazolel, SiliaMetS TAAcOH and SiliaMetS TAAcONa.

12. The process of claim 1, wherein step (d) is performed in an organic solvent selected from the group consisting of tetrahydrofuran (THF), acetonitrile (MeCN), ethanol, 2-methyl tetrahydrofuran (Me-THF), toluene (PhMe), and combinations thereof, and optionally combined with water.

13. The process of claim 1, wherein the step (d) is performed in the presence of a base selected from the group consisting of sodium carbonate, potassium carbonate, sodium phosphate, potassium phosphate, sodium bicarbonate, potassium bicarbonate, and combinations thereof, and optionally steps (a) to (d) are conducted in one reaction vessel.

14. The process of claim 1, further comprising a conversion of abiraterone of formula (I) into abiraterone acetate of formula (I')

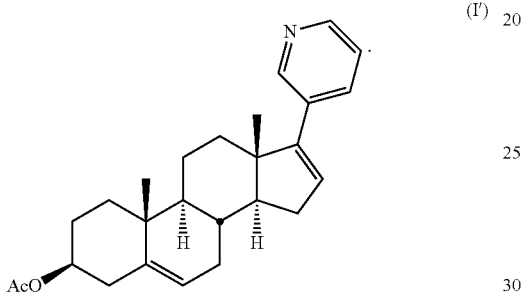

Figure 2:
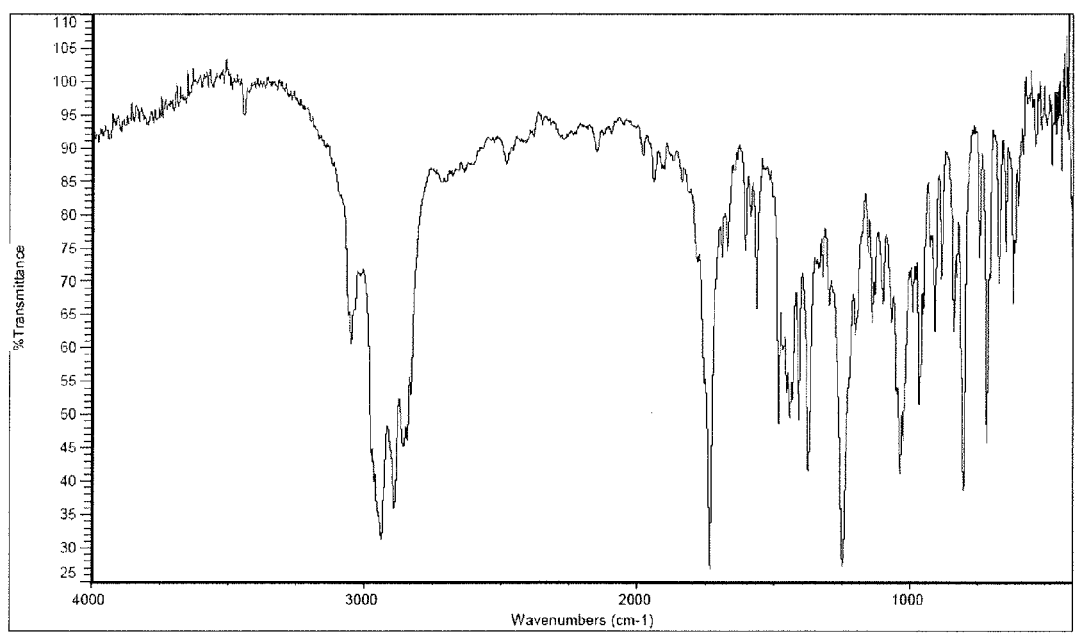
FIG. 2 is the schematic diagram showing the IR spectrum of abiraterone acetate of formula (I').
Figure 3:
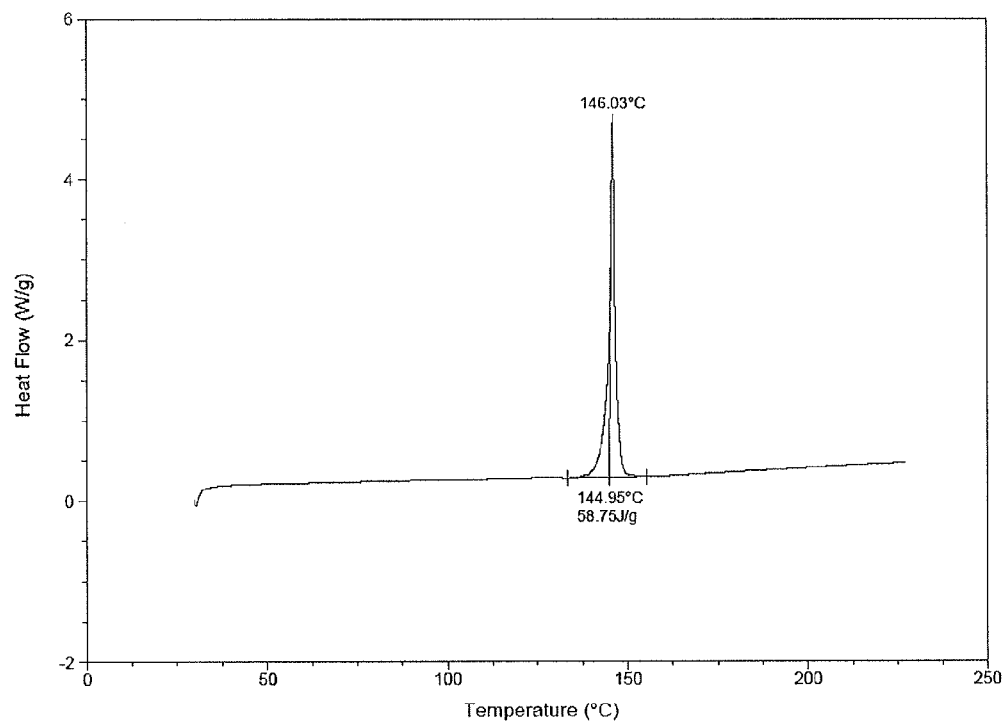
FIG. 3 is the schematic diagram showing the DSC curve of abiraterone acetate of formula (I').
Figure 4:
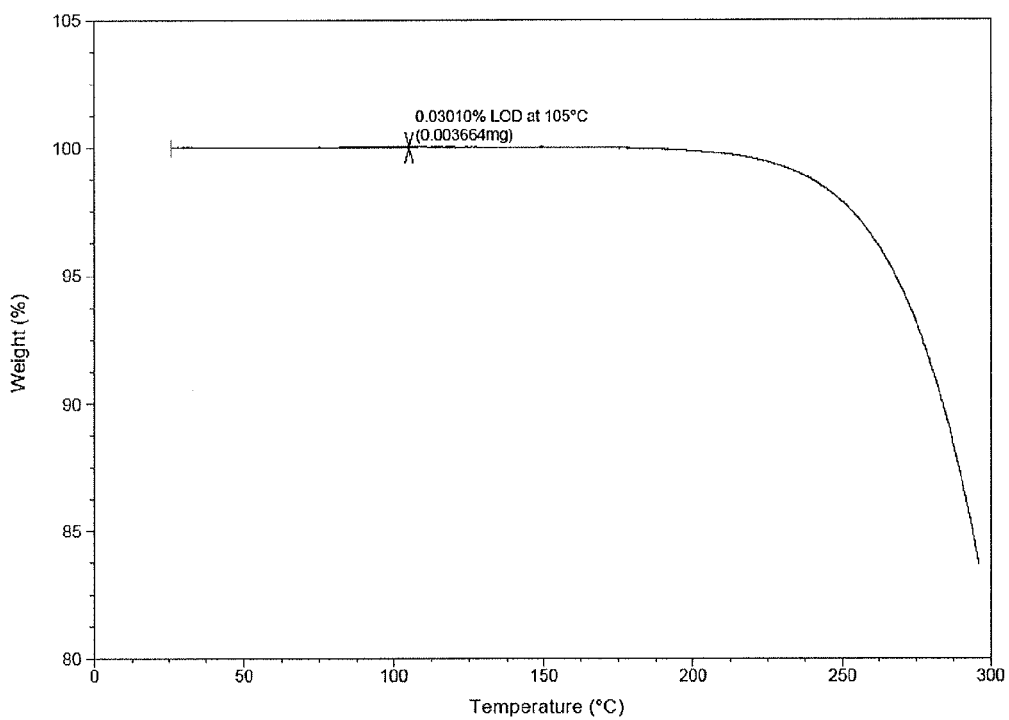
FIG. 4 is the schematic diagram showing the TGA curve of abiraterone acetate of formula (I').
Figure 5:
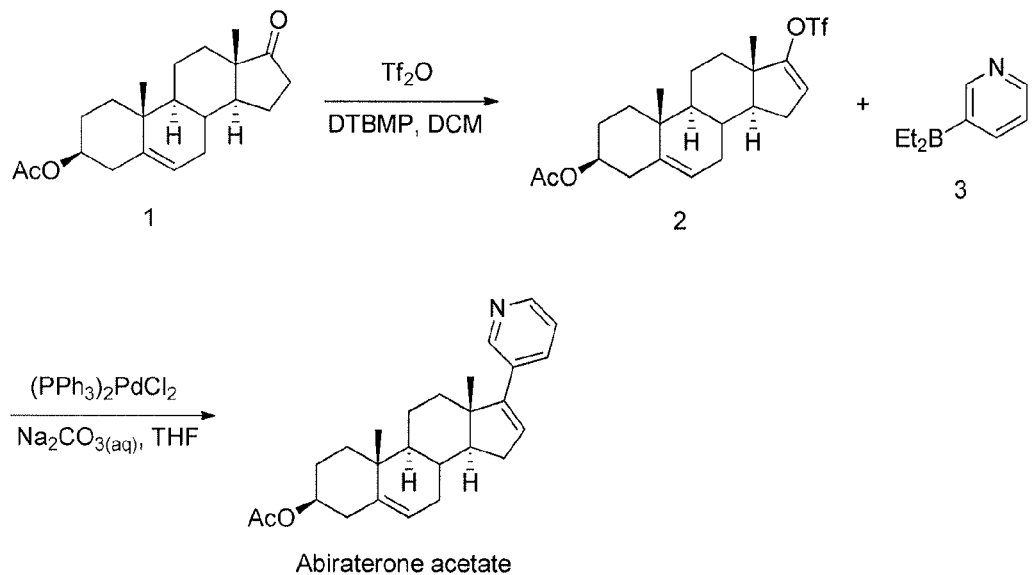
FIG. 5 provides Scheme 1 illustrating a synthetic route shown in U.S. Pat. No. 5,604,213.
Figure 6:
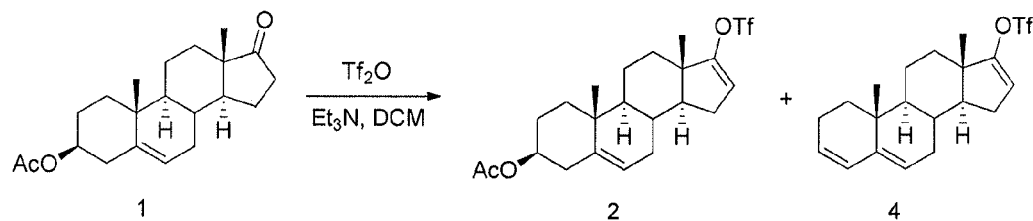
FIG. 6 provides Scheme 2 illustrating the preparation of vinyl triflate 2 shown in WO2006021776A1.
Figure 7:
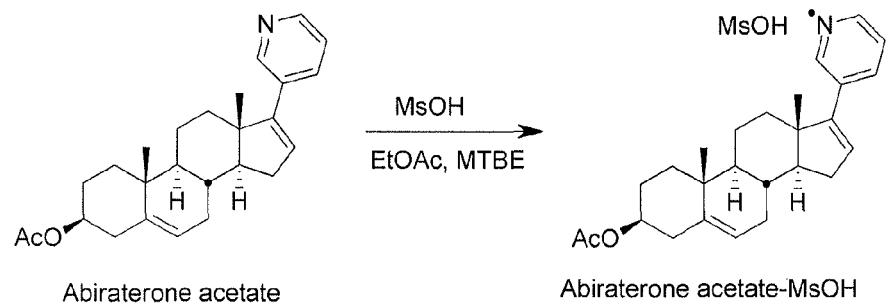
FIG. 7 provides Scheme 3 illustrating formation of abiraterone acetate MsOH salt shown in WO2006021776A1.
Figure 8:
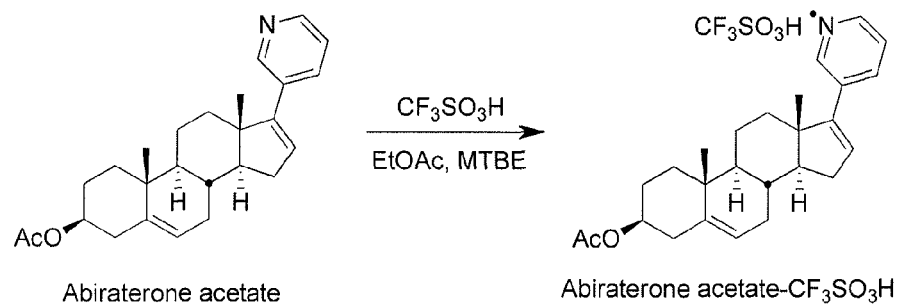
FIG. 8 provides Scheme 4 illustrating the formation of abiraterone acetate CF$_3$SO$_3$H salt as shown in CN102030798A.
Figure 9:
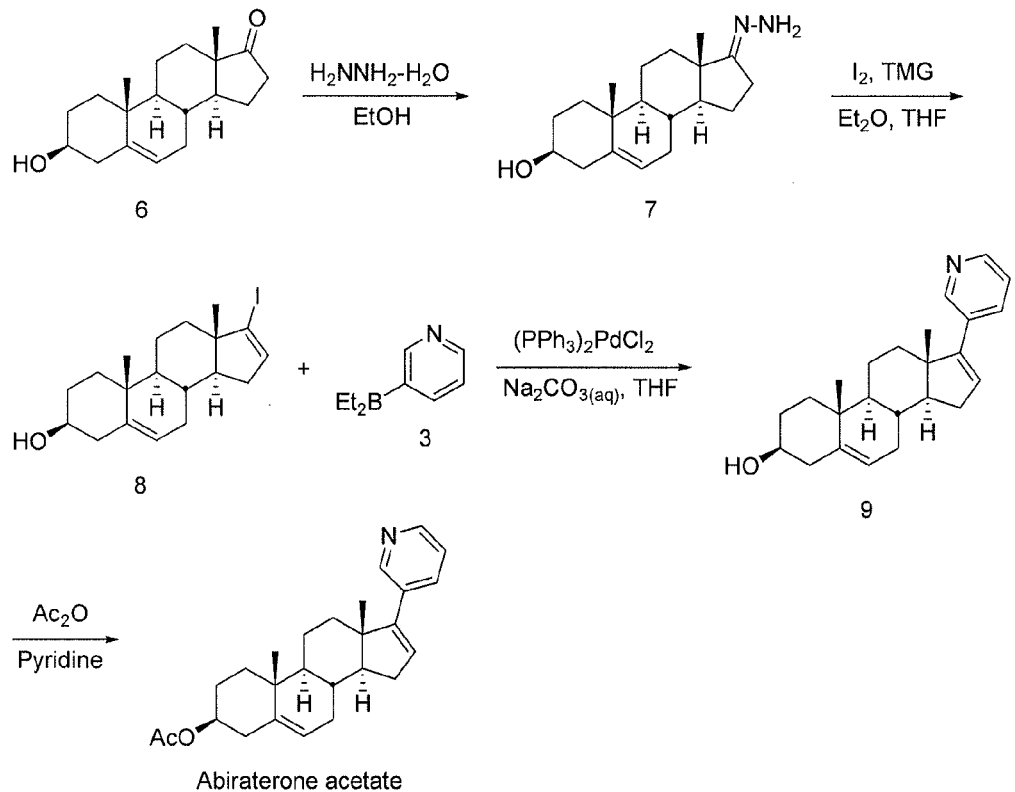
FIG. 9 provides Scheme 5 illustrating a synthetic route shown in U.S. Pat. No. 5,604,213.
Figure 10:
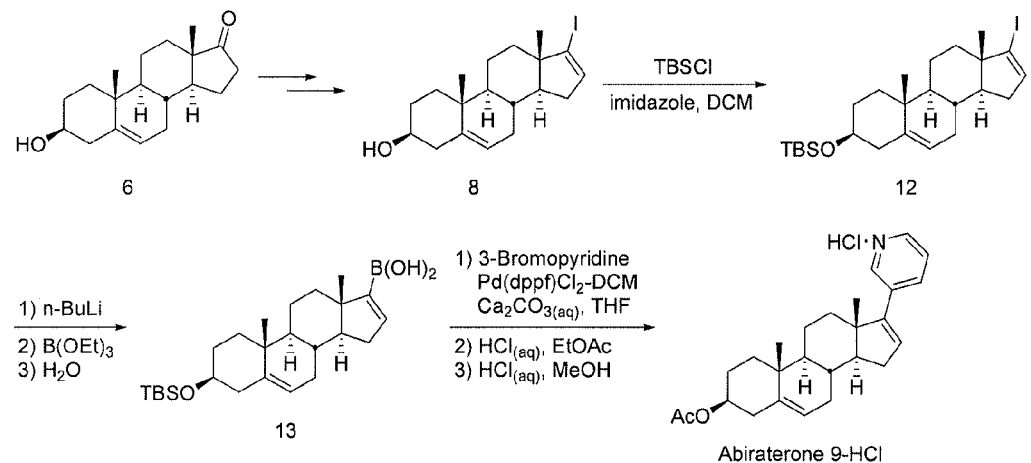
FIG. 10 provides Scheme 6 illustrating the synthetic route shown in WO2013030410A2.
Figure 11:
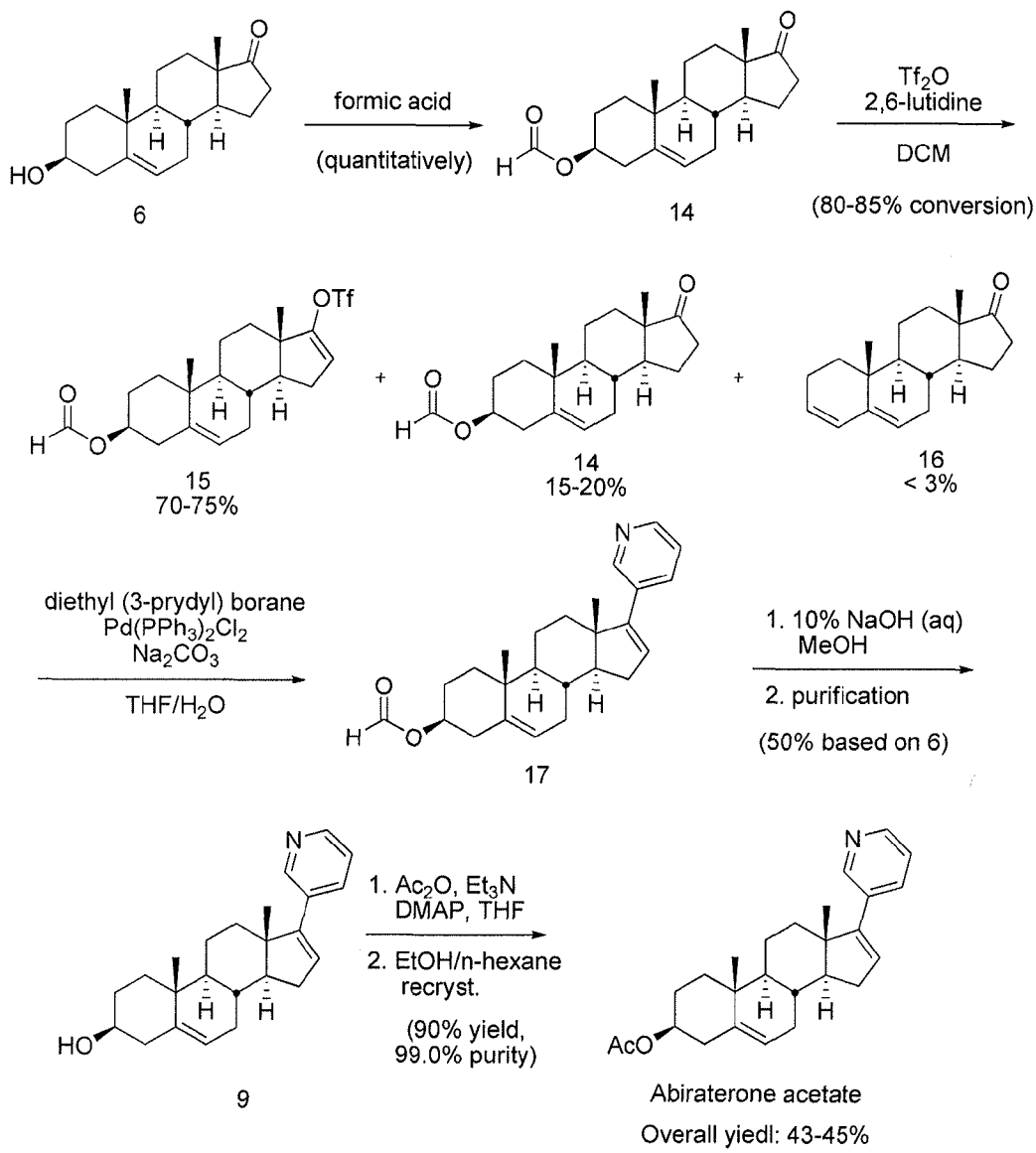
FIG. 11 provides Scheme 7 illustrating the synthetic route shown in WO2013053691A1.
Figure 12:
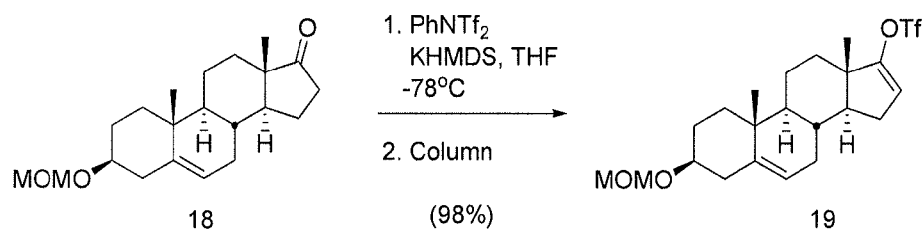
FIG. 12 provides Scheme 8 illustrating the synthetic route shown in *Steroids*, 2010, 75, 936-943.

15. The process of claim 14, wherein the conversion further comprises:

providing a solution of abiraterone acetate in an organic solvent selected from the group consisting of n-hexane, n-heptane, cyclohexane, acetone, acetonitrile (MeCN), dimethylsulfoxide (DMSO), methanol, ethanol, and combinations thereof;

heating the solution;

isolating the crystalline form of abiraterone acetate, and drying the isolated crystalline form of abiraterone acetate;

wherein (a) the crystalline form of abiraterone acetate is characterized by a powder X-ray diffraction pattern with peaks at about 5.8°, 12.1°, 14.8°, 15.1°, 15.9°, 18.4°, 18.9°, 21.7°, 22.4°, and 23.0°±0.2 degrees in 2-theta;

(b) the crystalline form of abiraterone acetate exhibits an infrared absorption spectrum substantially identical to the spectrum shown in FIG. 2;

(c) the crystalline form of abiraterone acetate exhibits a DSC curve substantially identical to the curve shown in FIG. 3; or (d) the crystalline form of abiraterone acetate exhibits a TGA curve substantially to the curve shown in FIG. 4.

16. The process of claim 15, wherein the organic solvent is optionally combined with water.

17. The process of claim 15, wherein the powder X-ray diffraction pattern is substantially identical to the pattern shown in FIG. 1.

* * * * *